United States Patent [19]
Oka et al.

[11] 3,984,379
[45] Oct. 5, 1976

[54] PROCESS FOR PREPARATION OF POLYESTERS

[75] Inventors: Isao Oka; Takeo Shima; Takanori Urasaki; Takayuki Kobayashi; Kazuyoshi Suzuki, all of Iwakuni, Japan

[73] Assignee: Teijin Limited, Osaka, Japan

[22] Filed: July 11, 1974

[21] Appl. No.: 487,620

Related U.S. Application Data

[63] Continuation of Ser. No. 311,562, Dec. 4, 1972, abandoned.

[30] Foreign Application Priority Data
Dec. 6, 1971    Japan................................ 46-98501
Jan. 10, 1972   Japan................................ 47-4671

[52] U.S. Cl. ............................ 260/75 M; 260/75 R
[51] Int. Cl.² ................... C08G 63/26; C08G 63/30
[58] Field of Search ....................... 260/75 R, 75 M

[56] References Cited
UNITED STATES PATENTS
3,444,141   5/1969    Shima.............................. 260/75 M
3,518,226   6/1970    Wood .............................. 260/45.95
3,701,757   10/1972   Lazarus et al..................... 260/75 R
3,714,125   1/1973    Shima et al. ..................... 260/75 M
3,787,370   1/1974    Shima et al. ..................... 260/75 R Primary Examiner—Murray Tillman
Assistant Examiner—W. C. Danison, Jr.
Attorney, Agent, or Firm—Sherman & Shalloway

[57] ABSTRACT

According to this invention, during the formation of a fiber-forming polyester by the reaction of a dicarboxylic acid or its functional derivative with a glycol, an aromatic ortho-ester such as hexaphenyl ortho terephthalate is added to the molten polyester whereby a fiber-forming polyester of a low content of free carboxyl groups and diethylene glycol units is prepared. Moreover, the reaction rate of the polycondensation is greatly increased by selecting and using a suitable aromatic ortho-ester and thus there can be obtained a fiber-forming polyester of a very high molecular weight.

10 Claims, No Drawings

PROCESS FOR PREPARATION OF POLYESTERS

This is a continuation of application Ser. No. 311,562, filed Dec. 4, 1972, now abandoned.

This invention relates to an improvement of a process for the preparation of polyesters by melt polymerization of solid state polymerization. More detailedly, this invention relates to a process for the preparation of substantially linear, fiber-forming or film-forming polyesters from a dicarboxylic acid or its functional derivative (which will be referred to simply as "dicarboxylic acid component" hereinbelow) or a hydroxycarboxylic acid or its functional derivative (which will be referred to simply as "hydroxycarboxylic acid component" hereinbelow) and a glycol, such process being characterized by addition of an aromatic orthoester at a certain stage of the melt polycondensation reaction to thereby form polyesters having a low free carboxyl group content and a low diethylene glycol unit content.

It has been well-known in the art that polyesters are prepared from a dicarboxylic acid and a dihydric alcohol. More specifically, it has been known that polyesters are formed by the reaction between a glycol (dihydric alcohol) and at least one member selected from aliphatic dicarboxylic acids of 4 – 20 carbon atoms such as succinic acid, adipic acid and sebacic acid and aromatic dicarboxylic acids such as terephthalic acid, isophthalic acid, diphenyl-4,4'-dicarboxylic acid, naphthalene-2,6-dicarboxylic acid, diphenylether-4,4'-dicarboxylic acid, diphenylsulfone-4,4'-dicarboxylic acid, diphenylmethane-4,4'-dicarboxylic acid and diphenoxyethane-4,4'-dicarboxylic acid; and that these polyesters are useful as starting materials of fibers or films.

As the glycol there are used one or more members selected from 1,2-glycols which are aliphatic or alicyclic dihydric alcohols containing hydroxyl groups bonded to adjacent carbon atoms, such as ethylene glycol, propylene glycol, butane-1,2-diol, cyclohexane-1,2-diol and cyclopentane-1,2-diol; 1,3-glycols which are aliphatic or alicyclic dihydric alcohols having alcoholic hydroxyl groups bonded to the carbon atoms at the 1- and 3-positions, such as trimethylene glycol, neopentylene glycol, butane-1,3-diol and cyclohexane-1,3-diol; and other glycols such as tetramethylene glycol, hexamethylene glycol, decamethylene glycol, cyclohexane-1,4-diol, cyclohexane-1,4-dimethanol and para-xylylene glycol. Among these glycols, 1,2-glycols may be used also in the form of a reactive derivative such as a carbonic acid ester or anhydride.

Polyesters composed of the above-mentioned dicarboxylic acid and glycol are prepared by a two-stage method comprising the first step of forming a precondensate by the direct esterification reaction between the dicarboxylic acid and glycol, the ester exchange reaction between a functional derivative, such as a lower alkyl or phenyl ester, of the dicarboxylic acid and the glycol, or the addition reaction between the dicarboxylic acid and an alkylene oxide; and the second step of forming a high polymer by heating the precondensate at a reduce pressure and/or in an inert gas current to thereby remove the glycol.

In this specification, the above-mentioned dicarboxylic acids and their functional derivatives such as alkyl esters and phenyl esters are inclusively indicated by the term "dicarboxylic acid component".

There has also been known a method of preparing polyesters comprising reacting a hydroxycarboxylic acid such as ω-hydroxycaproic acid, p-hydroxybenzoic acid, p-(β-hydroxyethoxy)benzoic acid, p-4-(β-hydroxyethoxy)-phenylbenzoic acid and β-hydroxyethoxyvanillic acid or a functional derivative thereof such as lower aliphatic esters and phenyl esters, with a glycol such as recited above or a reactive derivative thereof, to form a glycol ester or a lower polymer, and polycondensing the same to form a substantially linear, film-forming or fiber-forming polyester.

The above-mentioned hydroxycarboxylic acids and their functional derivatives are inclusively indicated by the term "hydroxycarboxylic acid component" in this specification.

The polycondensation of the ester or low polyester formed by the reaction between the dicarboxylic acid component or hydroxycarboxylic acid component and the glycol component is conducted with removal of the glycol. This polycondensation reaction is allowed to advance even in the absence of a catalyst, but the reaction rate is extremely low in this case. Accordingly, the rate of the polycondensation reaction is generally increased by employing such catalysts as antimony trioxide, antimony acetate, antimony trifluoride, antimony glycolate, tetrabutyl titanate, tetrapropyl titanate, potassium ethyl titanate ($K_2Ti(OC_2H_5)_6$), germanium dioxide, tetrabutyl germanate ($Ge(OC_4H_9)_4$), zinc acetate, lead oxide and manganese acetate. However, it takes a considerably long time to complete this polycondensation reaction even with use of such catalysts, and it is necessary to conduct the reaction at such high temperatures as 200° – 350°C. Therefore, occurrence of side reactions such as thermal decomposition cannot be avoided, resulting in increase of the amount of terminal carboxyl groups and in formation of polyesters having poor heat stability. For instance, when polyethylene terephthalate is prepared on a commercial scale, it is necessary to carry out the reaction at such high temperatures as ranging from 270°C. to 290°C. under such a high vacuum as 0.1 mm Hg for 2 – 10 hours. In order to maintain the output at a certain level it is necessary to provide large equipments. Further, since the reactants are exposed to high temperatures for a long time, side reactions such as thermal decomposition are caused to advance together with the polycondensation reaction, it is considerably difficult to reduce the content of terminal carboxyl groups below a certain limit and to obtain a polymer having a degree of polymerization exceeding a certain level.

As the process solving the above problem, there have been proposed a process in which the polycondensation reaction is carried out in the presence of an alkyl orthoester (Japanese Patent Application Laid-Open Specification No. 16598/72) and a process in which the polycondensation reaction is carried out in the presence of an ortho-carbonate (U.S. Pat. Nos. 3,714,125 and 3,787,370, and Dutch Patent Application Laid-Open Specifications Nos. 71-03731 and 72-03605).

However, in the process in which the polycondensation reaction is conducted in the presence of an alkyl orthocarbonate, the polycondensation reaction is not sufficiently promoted, and such process is also defective in that it is difficult to obtain a polymer having a degree of polymerization exceeding a certain level.

In case the polycondensation reaction is carried out in the presence of an aryl ortho-carbonate, it is possible to reduce the free carboxyl group content (the terminal carboxyl group content) of the resulting polycondensate, and the rate of the polymerization reaction can be greatly increased by adjusting the amount of the orthocarbonate added within a suitable range.

However, in this process in which the polycondensation reaction is carried out in the presence of an aryl orthocarbonate, formation of diethylene glycol units as by-products owing to the addition of the aryl ortho-carbonate cannot be avoided. Especially when the aryl ortho-carbonate is used in a greater amount for further reducing the free carboxyl group content in the resulting polycondensate, considerable amounts of diethylene glycol units are formed as by-products and are incorporated in the resulting polycondensate, which results is reduction of the oxidation stability of the polycondensate.

It is therefore a primary object of this invention to provide a promoter for the polycondensation reaction which can reduce the terminal carboxyl group content in the resulting polycondensate and which hardly causes formation of diethylene glycol units as by-products.

Another object of this invention is to provide a process for the preparation of fiber-forming or film-forming polyesters wherein the rate of the polycondensation reaction is increased and intended products are obtainable by a rapid polycondensation reaction.

Still another object of this invention is to provide a process according to which polyesters are obtained having high degree of polymerization, that is a high molecular weight, as can rarely be obtained by conventional techniques.

Other objects and advantages of this invention will be apparent from the description given hereinbelow.

The objects and advantages of this invention can be attained by a process for the preparation of substantially linear, highly polymerized carboxylic acid esters by removing the glycol from a glycol ester of a dicarboxylic or hydroxycarboxylic acid or its low condensate, the to thereby effect the polycondensation, which process comprises adding an aromatic ortho-ester expressed by the general formula

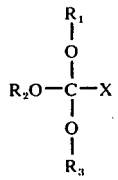

(I)

wherein

X is selected from the group consisting of R,

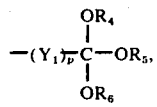

$-(Y_2)_p$ COOR$_7$ or $-Y_3-O-Z$; Z is selected from the group consisting of

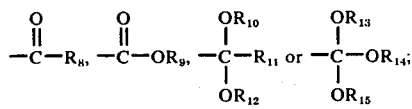

R, $R_8$ and $R_{11}$, which may be the same or different, stand for a hydrogen atom or a mono-valent organic group being inert to an ester-forming component and having a molecular weight not exceeding 250; $R_1$, $R_2$, $R_3$, $R_4$, $R_5$, $R_6$, $R_7$, $R_9$, $R_{10}$, $R_{12}$, $R_{13}$, $R_{14}$ and $R_{15}$, which may be the same or different, stand for a mono-valent organic group being inert to an ester-forming component and having a molecular weight not exceeding 250; at least one of the group $R_1$, $R_2$, $R_3$, $R_4$, $R_5$ and $R_6$, at least one of the group $R_1$, $R_2$, $R_3$, $R_{10}$ and $R_{12}$, and at least one of the group $R_1$, $R_2$, $R_3$, $R_{13}$, $R_{14}$ and $R_{15}$ stand for a mono-valent aromatic group; in case the ortho-ester expressed by the above formula contains R, $R_7$, $R_8$ and $R_9$, at least one of $R_1$, $R_2$ and $R_3$ is a mono-valent aromatic group; two of $R_1$, $R_2$ and $R_3$, two of $R_4$, $R_5$ and $R_6$, two of $R_{10}$, $R_{11}$ and $R_{12}$, and two of $R_{13}$, $R_{14}$ and $R_{15}$ may be bonded together to form a ring; $Y_1$, $Y_2$ and $Y_3$, which may be the same or different, stand for a divalent organic radical inert to an ester-forming component; and $p$ is 0 or 1,
to a molten polyester and conducting the polycondensation under conditions such that the reaction mixture is maintained in the molten or solid state.

The value of intrinsic viscosity used in the specification and claims is one calculated from the value measured in orthochlorophenol at 35°C.

This invention will now be described in detail.

As the dicarboxylic acid component or hydroxycarboxylic acid component, there may be used any member selected from the above-mentioned compounds, and any of the glycols or reactive derivatives thereof recited hereinabove may be used as the glycol component.

In this invention there may be used any of the known catalysts used in the polycondensation step of the ester-forming reaction, inclusive of those mentioned hereinabove, in conducting the polycondensation of lowly polymerized polyesters.

Any conventional process for polyester preparation may be adopted for forming the polyesters of this invention, using the dicarboxylic acid or hydroxycarboxylic acid component and the glycol or its reactive derivative. Not only may the above-mentioned known catalysts may be used at the polycondensation reaction stage but also at the stage of forming from the dicarboxylic acid or hydroxycarboxylic acid component and the glycol or its reactive derivative a glycol ester of said acid or a low condensate thereof, there may be used known catalysts such as conventional ester exchange reaction catalysts. Further, in order to prevent decomposition of the reaction product during the polycondensation reaction, it is possible to add to the reaction mixture a stabilizer such as phosphorous acid, phosphoric acid, and derivatives thereof, and/or a delustering agent such as titanium oxide.

Still further, in order to copolymerize a monofunctional compound such as benzoic acid, benzoyl benzoic acid and alkoxypolyalkylene glycols with the ends of the resulting polyester or to copolymerize a trifunctional or more highly functional compound such as glycerin, pentaerythritol, benzene tetracarboxylic acid, hydroxyisophthalic acid and pyromellitic acid, with the ends of the resulting polyester, it is possible to add such monofunctional or polyfunctional compounds in small quantities to the reaction system at the polycondensation stage.

In this invention, at the stage of polycondensing a low polymeric polyester, an aromatic ortho-ester expressed by the above general formula (I) may be added to the melt of the polycondensation reaction product (polyester) when the intrinsic viscosity of the polycondensation reaction product reaches preferably at least 0.2 and more preferably at least 0.3. The polycondensation reaction is then further continued until a polyester of a desired intrinsic viscosity is obtained.

Any of compounds expressed by the above general formula (I) may be added as the aromatic ortho-ester in this invention. In the definition of symbols R, $R_1$ to $R_{15}$ and $Y_1$ to $Y_3$ appearing in the general formula (I), the expression "inert to an ester-forming component" means that such groups have no functional substituent capable of forming an ester under the conditions of the polyester-forming reaction intended in this invention. More specifically, none of groups R, $R_1$ to $R_{15}$ and $Y_1$ to $Y_3$ constituting the aromatic orthoester of the general formula (I) should have an ester-forming functional substituent such as a carboxyl (—COOH) group, an alkoxycarbonyl (—COOR$_{16}$ in which R$_{16}$ is a monovalent hydrocarbon residue) group, a hydroxyl (—OH) group or an acyloxy (—OCOR$_{16}$ in which R$_{16}$ is as defined above) group.

The reasons why in the above general formula (I) it is specified that each of R and $R_1$ to $R_{15}$ has a molecular weight not exceeding 250 is that when one or more of these groups have a molecular weight exceeding 250, though the intended effect of reducing the free carboxyl group content in the resulting polyester is attained more or less, the amount (weight) of the aromatic ortho-ester to be added should be increased because of the high molecular weight, which results in economical disadvantages. Moreover because products formed by the decomposition of the aromatic orthoester of such high molecular weight are difficult to remove from the polycondensation system by distillation, reduction of the molecular weight in the resulting polyester sometimes occurs.

Accordingly, in this invention it is particularly preferred that each of R and $R_1$ to $R_{15}$ has a molecular weight not exceeding 200.

As examples of groups R and $R_1$ to $R_{15}$, we can mention mono-valent aliphatic groups such, as: methyl, ethyl, n-propyl, iso-propyl, n-butyl, iso-butyl, tert-butyl, cyclohexyl, 4-methylcyclohexyl, cyclopentyl, n-octyl, n-decyl, n-dodecyl, benzyl, phenethyl, α-naphthylmethyl, 2-(α-naphthyl)-ethyl, chloromethyl, dichloromethyl, trichloromethyl, 4-chlorophenethyl, 4-nitrophenethyl and 4-methoxyphenethyl groups; and mono-valent aromatic groups such, for instance, as phenyl, p-tolyl, m-tolyl, o-tolyl, p-iso-propylphenyl, p-tert-butylphenyl, p-ethylphenyl, p-n-octylphenyl, 3-methyl-4-ethylphenyl, p-cyclohexylphenyl, p-benzylphenyl, p-phenoxyphenyl, m-methoxyphenyl, p-methoxyphenyl, o-methoxyphenyl, p-nitrophenyl, p-chlorophenyl, p-bromophenyl, o-bromophenyl, α-naphthyl, β-naphthyl, 4-methylnaphthyl, p-phenylphenyl and o-phenylphenyl groups.

In the above general formula (I), two of $R_1$, $R_2$ and $R_3$, two of $R_4$, $R_5$ and R, two of $R_{10}$, $R_{11}$ and $R_{12}$, and two of $R_{13}$, $R_{14}$ and $R_{15}$ may be bonded together to form a ring. As examples of such a ring, we can mention divalent alkylene and arylene groups such as: ethylene, 1,2-propylene, chloromethylethylene, 1,3-propylene, 1,2-butylene, iso-butylene, 1,4-butylene, 1,2-cyclohexylene, 1,2-cyclopentylene, 1,2-hexylene, o-phenylene and 2,3-naphthylene groups.

Among these groups, R, $R_8$ and $R_{11}$ may be a hydrogen atom.

Examples of the groups expressed by symbols $Y_1$, $Y_2$ and $Y_3$ include alkylene and arylene groups such as ethylene, 1,2-propylene, chloromethylethylene, 1,3-propylene, 1,2-butylene, iso-butylene, 1,4-butylene, 1,2-cyclohexylene, 1,4-cyclohexylene, 1,2-cyclopentylene, 1,3-cyclopentylene, 1,6-hexylene, 1,10-decylene, p-phenylene, m-phenylene, 4,4'-diphenylene, 2,6-naphthylene, 2,7-naphthylene, 1,5-naphthylene, 1,4-naphthylene,

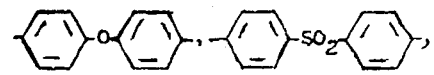

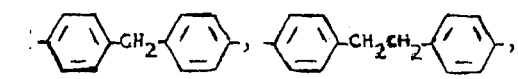

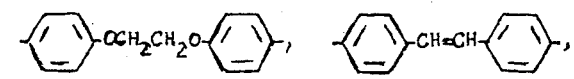

p-2,5-dibromophenylene, 2-methyl-p-phenylene, 4-methyl-m-phenylene,  and

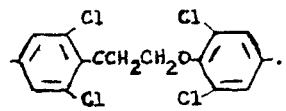

The groups $Y_1$, $Y_2$ and $Y_3$ may be or may not be present in the above general formula.

Preferable examples of the aromatic ortho-ester to be used in this invention will now be mentioned.

1. Compounds of the following formula (X in the general formula is a hydrogen atom):

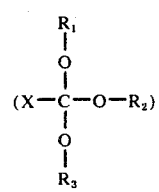

a. All of $R_1$, $R_2$ and $R_3$ are aromatic groups:
triphenyl ortho-formate
tricresyl ortho-formate
tri-(p-chlorophenyl) ortho-formate
tri-(α-naphthyl) ortho-formate di-(α-naphthyl)-mono-(p-phenylphenyl) ortho-formate b. One or two of $R_1$, $R_2$ and $R_3$ are aliphatic groups:
di-(p-chlorophenyl)-monoethyl ortho-formate
dibutyl-monophenyl ortho-formate
dihexyl-mono-(p-phenylphenyl) ortho-formate
di-(p-nitrophenyl)-monoethyl ortho-formate c. Two of $R_1$, $R_2$ and $R_3$ are bonded together to form a ring:
ethylphenyl ortho-formate

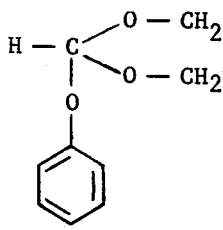

propylene-(p-phenylphenyl) ortho-formate

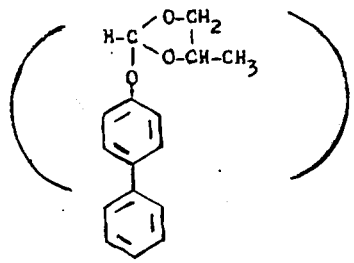

o-phenylene-phenyl ortho-formate

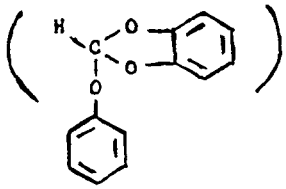

o-phenylene-n-butyl ortho-formate

2. Compounds of the following formula (in the general formula, X is a group —R and R is a mono-valent organic group):

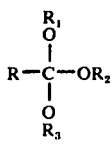

a. All of $R_1$, $R_2$ and $R_3$ are mono-valent aromatic groups:
triphenyl ortho-acetate
tricresyl ortho-acetate
diphenylcresyl ortho-acetate
tri-α-naphthyl ortho-acetate
tri-β-naphthyl ortho-acetate
triphenyl ortho-chloroacetate
triphenyl ortho-trichloroacetate
tri-p-chlorophenyl ortho-propionate
tri-(p-tert-butylphenyl) ortho-benzoate
tri-(p-octylphenyl) ortho-benzoate
mono-(p-octylphenyl)-mono-p-chlorophenyl-monophenyl orthoacetate
tri-(p-tert-butylphenyl) ortho-benzoate
β-[tri-(2,4-dibromophenyl)] ortho-naphthoate
tri-(p-tert-butylphenyl) ortho-m-bromobenzoate b. One or two of $R_1$, $R_2$ and $R_3$ are aliphatic groups:
monophenyl-diethyl ortho-acetate
monomethyl-di-(p-tolyl) ortho-m-bromobenzoate
mono-(p-octylphenyl)-monomethyl-monooctyl ortho-acetate
mono-(p-nitrophenyl)-di-(n-propyl) ortho-β-naphthoate
mono-α-naphthyl-diethyl ortho-p-phenylbenzoate
diphenyl-monooctyl ortho-chloroacetate c. Two of $R_1$, $R_2$ and $R_3$ are bonded together to form a ring:
ethylene-phenyl ortho-acetate
1,2-propylene-1-(4-chloro)-naphthyl ortho-p-toluylate
1,2-propylene-(4-tert.-butyl)phenyl ortho-p-toluylate
2,3-butylene-p-phenylphenyl ortho-propionate
1,1,2,2-tetramethylene-p-tert-butylphenyl ortho-acetate

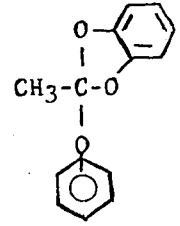

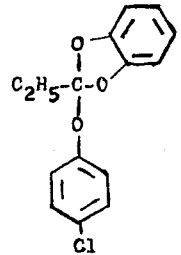

3. Compounds of the following formula (in the general formula

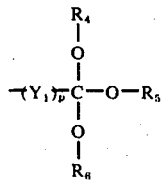

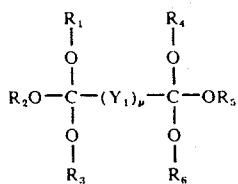

a. All of $R_1$ to $R_6$ are aromatic groups:
hexaphenyl ortho-oxalate
1,1-diphenoxy-1-tolyloxy-2,2-diphenoxy-2-tolyloxyethane
1,1-di-α-naphthoxy-1-phenoxy-2,2-di-α-naphthoxy-2-phenoxyethane
hexaphenyl ortho-terephthalate
hexacresyl ortho-terephthalate
hexa-β-naphthyl ortho-terephthalate
hexa-[2,4-di-(methylphenyl)]ortho-terephthalate
1,4-bis-(diphenoxy-mono-2,6-dichlorophenoxymethyl) benzene

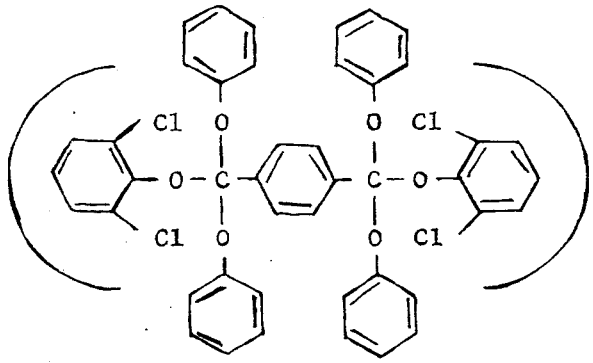

1,4-bis-(phenoxy-m-tolyloxy-β-naphthoxymethyl) benzene
1-(triphoxymethyl)-4-(tri-2,4-dimethylphenoxymethyl) benzene
hexaphenyl ortho-isophthalate
hexaphenyl-2,6-naphthalene ortho-carboxylate
hexacresyl-2,6-naphthalene ortho-carboxylate
2,6-bis-(diphenox-p-chlorophenoxymethyl) naphthalene
hexaphenyl-2,7-naphthalene ortho-carboxylate
2,7-bis-(diphenoxy-p-isopropylphenoxymethyl) naphthalene
2,7-bis-(phenoxy-p-tolyloxy-p-n-butylphenoxymethyl) naphthalene
hexatolyl-4,4'-diphenoxyethane ortho-carboxylate
hexa-(p-chlorophenyl)-4,4'-diphenylsulfone ortho-carboxylate b. $R_1$ to $R_6$ include aliphatic groups:
1,1-diphenoxy-1-methoxy-2,2-diphenoxy-2-methoxyethane
1,1-dimethoxy-1-p-tolyloxy-2,2-dimethoxy-2-p-tolyloxyethane
hexa-(2,4-dimethylphenyl) ortho-malonate
1,1-diphenoxy-1-cyclohexyloxy-3,3-diphenoxy-3-cyclohexyloxypropane
1,1-diphenoxy-1-benzyloxy-3,3-diphenoxy-3-benzyloxypropane
hexaphenyl ortho-adipate
1,1-di-p-chlorophenoxy-1-propoxy-6,6-di-p-chlorophenoxy-6-propoxyhexane
1,1-dimethoxy-1-α-naphthyloxy-6,6-dimethoxy-6-α-naphthyloxyhexane
1,4-bis-(methoxy-diphenoxmethyl) benzene
1,4-bis-(dimethoxy-phenoxymethyl) benzene
1,4-bis-(dimethoxy-p-chlorophenoxymethyl) benzene
1-(diphenoxy-ethoxymethyl)-4-(diphenoxy-butoxymethyl) benzene
1-(dimethoxy-phenoxymethyl)-4-(trimethoxymethyl) benzene
1-(triphenoxymethyl)-4-(triethoxymethyl) benzene
1-(triphenoxymethyl)-4-(diphenoxy-methoxymethyl) benzene
1,3-bis-(diphenoxy-methoxymethyl) benzene
2,6-bis-(dibutoxy-phenoxymethyl) naphthalene
2,6-bis-(methoxy-diphenoxymethyl) naphthalene c. Two of $R_1$, $R_2$ and $R_3$ and/or $R_4$, $R_5$ and $R_6$ are bonded together to form a ring:

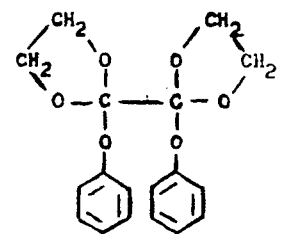

(bis-ethylenephenyl ortho-oxalate)

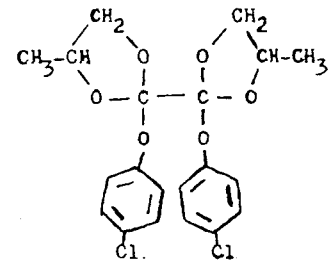

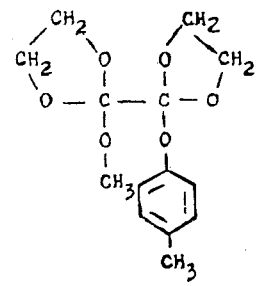

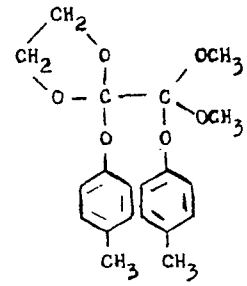

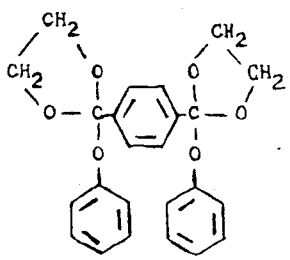

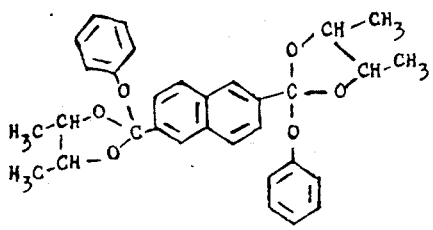

4. Compounds of the following formula (in the general formula X is a group $$-(Y_2)_p-\overset{O}{\underset{\|}{C}}-O-R_7):$$

$$R_2O-\overset{\overset{R_1}{|}}{\underset{\underset{R_3}{|}}{C}}-(Y_2)_p-\overset{O}{\underset{\|}{C}}O-R_7$$

a. All of $R_1$, $R_2$ and $R_3$ are aromatic groups:
phenyl triphenoxyacetate
tolyl tritolyloxyacetate
phenyl tri-(p-chlorophenox)-acetate
phenyl tri-(α-naphthoxy)-acetate
β-naphthyl tri-(p-butylphenoxy)-acetate
p-nitrophenyl diphenoxy-mono-(p-propylphenoxy)-acetate
phenyl α-phenoxy-α-(p-butylphenoxy)-α-(p-naphthoxy)-acetate
p-benzylphenyl triphenoxyacetate
ethyl tri-(phenylphenoxy)-acetate
phenyl p-triphenoxymethyl-benzoate
phenyl m-triphenoxymethyl-benzoate
p-phenylphenyl 6-[tri-(p-chlorophenoxy)methyl]-2-naphthoate
p-methoxyphenyl 7-[tri-(p-octylphenoxy)methyl]-2-naphthoate
p-butylphenyl 4'-[tri-(p-propylphenoxy)methyl]-4-diphenylcarboxylate b. One or two of $R_1$, $R_2$ and $R_3$ are aliphatic groups:
phenyl phenoxydiethoxyacetate
naphthyl p-propylphenoxy-dibutoxyacetate
p-phenoxyphenyl p-chlorophenoxy-di-isopropoxyacetate
octylphenyl di-(p-methoxyphenoxy)-n-hexoxyacetate
phenyl mono-p-chlorophenoxy-monophenoxy-monomethoxyacetate
phenyl 4-(phenoxydimethoxy)-methylbenzoate
methyl 4-(methoxy-di-p-naphthoxy)-methylbenzoate
p-benzylphenyl 3-(di-p-chlorophenoxy-m-propoxy)-methylbenzoate p-methoxyphenyl 4-[p-(di-p-nitrophenoxy-n-butoxy)-methyl]-phenylbenzoate c. Two of $R_1$, $R_2$ and $R_3$ are bonded together to form a ring:

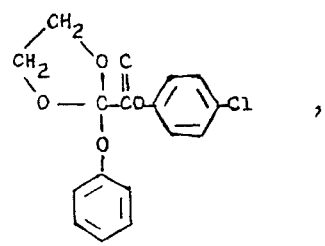

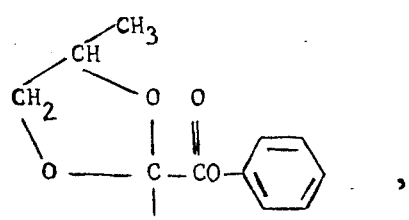

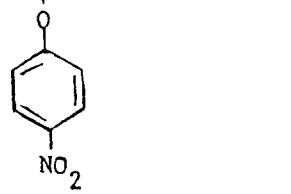

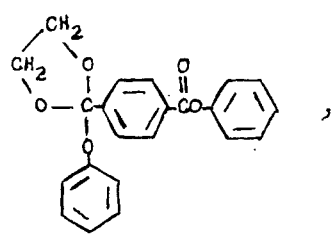

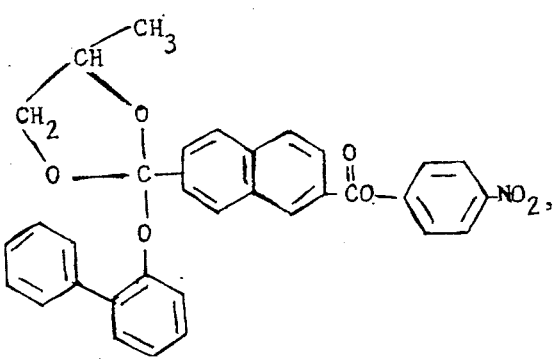

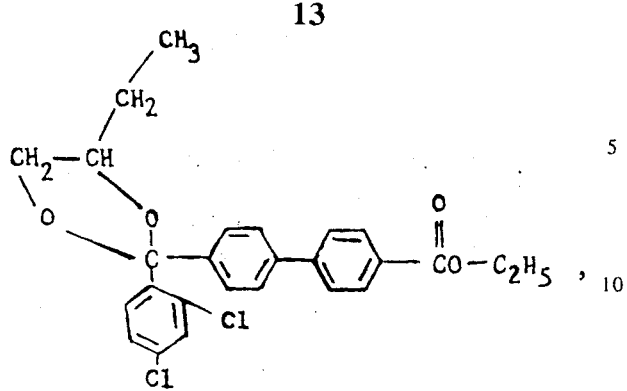

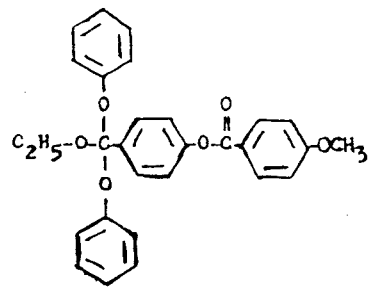

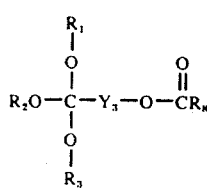

5. Compounds of the following formula (in the general formula X is —Y$_3$—O—Z and Z is

):

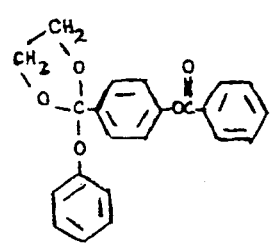

a. All of R$_1$, R$_2$ and R$_3$ are aromatic groups:
phenyl 4-acetyloxy-ortho-benzoate
p-cresyl 6-benzoyloxy-ortho-2-naphthoate
p-tert-butylphenyl p-formyloxy-ortho-benzoate
phenyl-di-(β-naphthyl) p-(β-naphthoxyloxy)-ortho-benzoate

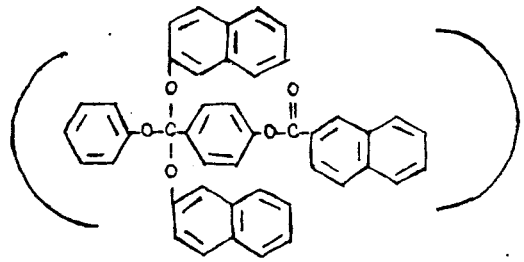

b. One or two of R$_1$, R$_2$ and R$_3$ are aliphatic groups:

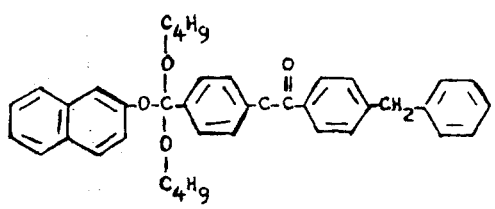

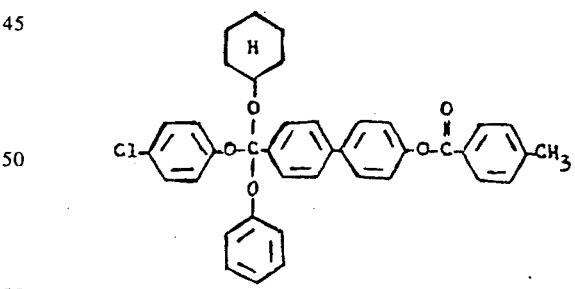

c. Two of R$_1$, R$_2$ and R$_3$ are bonded together to form a ring:

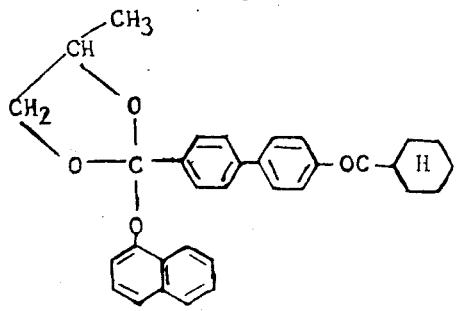

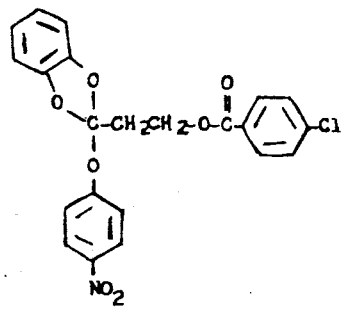

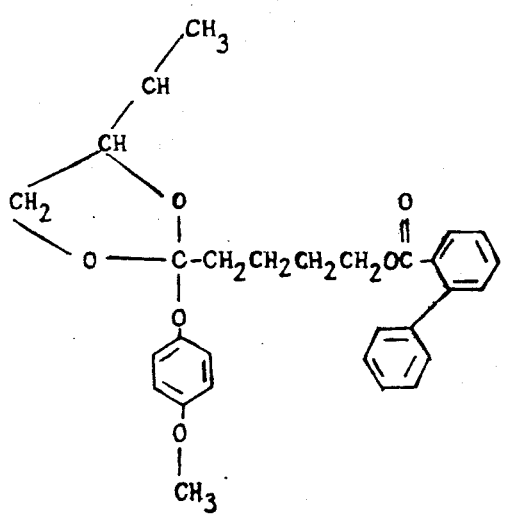

6. Compounds of the following formula (in the general formula X is —Y₃—O—Z and Z is

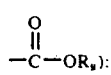

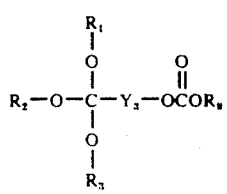

a. All of $R_1$, $R_2$ and $R_3$ are aromatic groups:
(2,2,2-triphenoxyethyl)-phenyl carbonate
[2-phenoxy-2,2-di-(p-tolyloxy)-ethyl]-phenyl carbonate
[p-tri-(phenoxy)-methylphenyl]-phenyl carbonate p-[(p-methoxyphenoxy)-di-(phenoxy)-methyl]-phenyl-n-amyl carbonate b. One or two of $R_1$, $R_2$ and $R_3$ are aliphatic groups:
[2,2-di-(phenoxy)-methoxyethyl]-p-chlorophenyl carbonate
[2,2,2-tri-(phenoxy)-ethyl]-methyl carbonate c. Two of $R_1$, $R_2$ and $R_3$ are bonded together to form a ring:

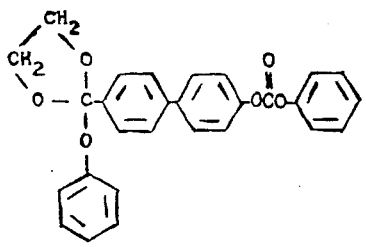

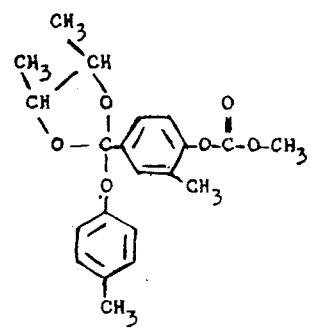

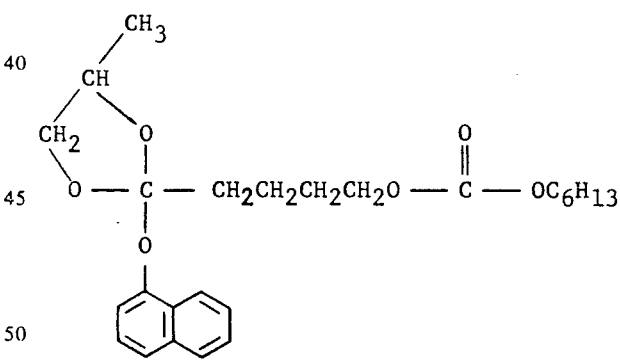

7. Compounds of the following formula (in the general formula X is —Y₃—O—Z and Z is

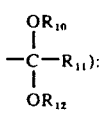

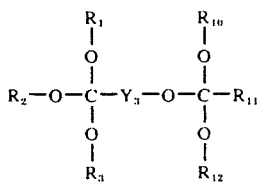

a. All of $R_1$, $R_2$, $R_3$, $R_{10}$ and $R_{12}$ are aromatic groups:
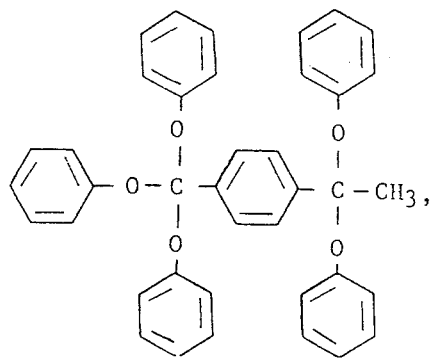
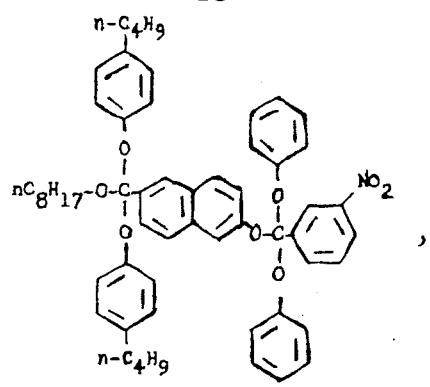
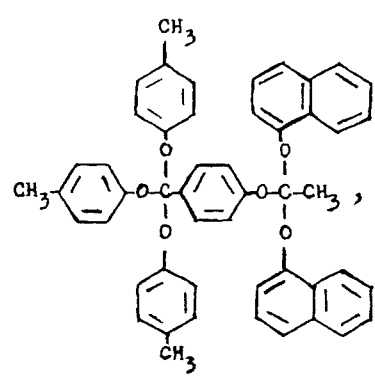
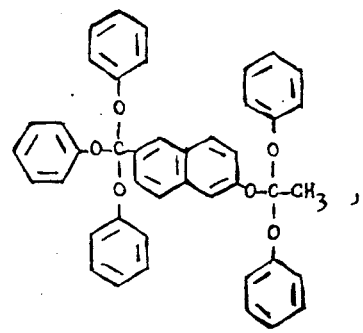
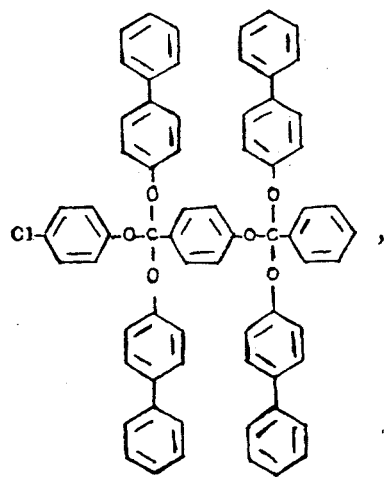
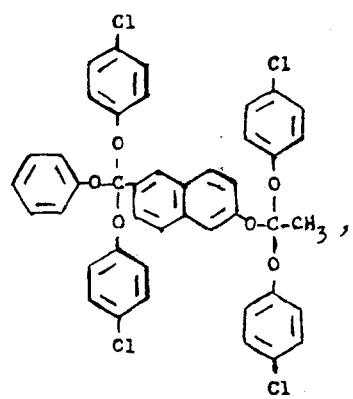
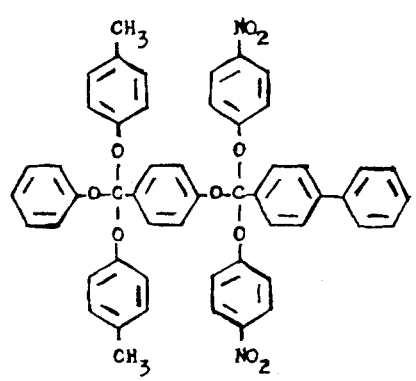
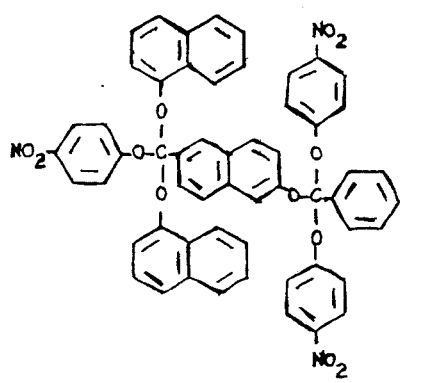

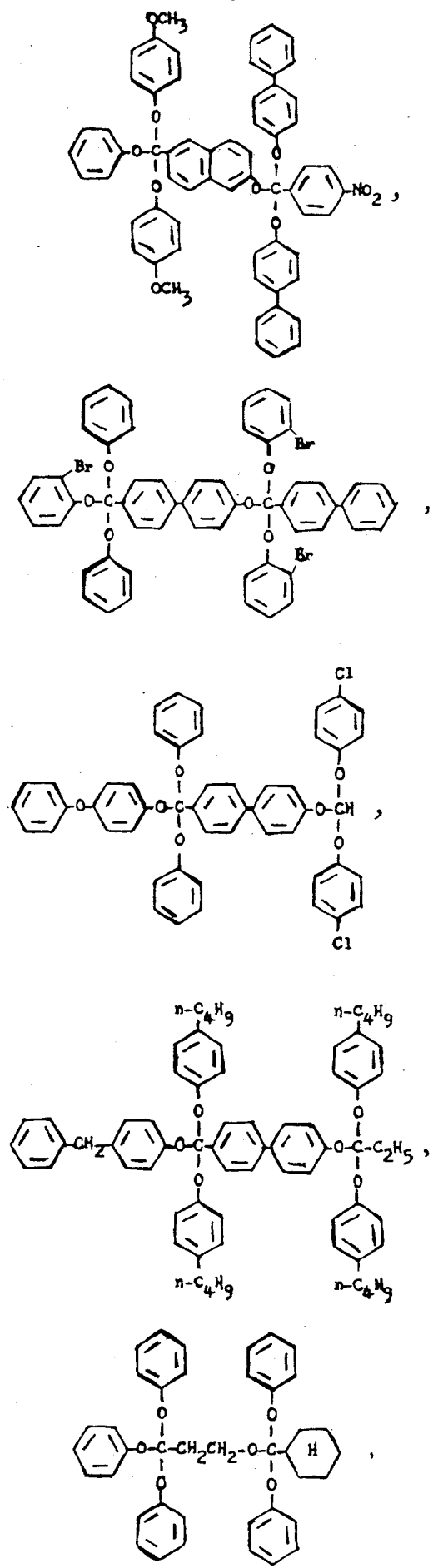

$R_1$, $R_2$, $R_3$, $R_{10}$ and $R_{12}$ include aliphatic groups:
c. Two of $R_1$, $R_2$ and $R_3$, and/or $R_{10}$ and $R_{11}$ are bonded together to form a ring:
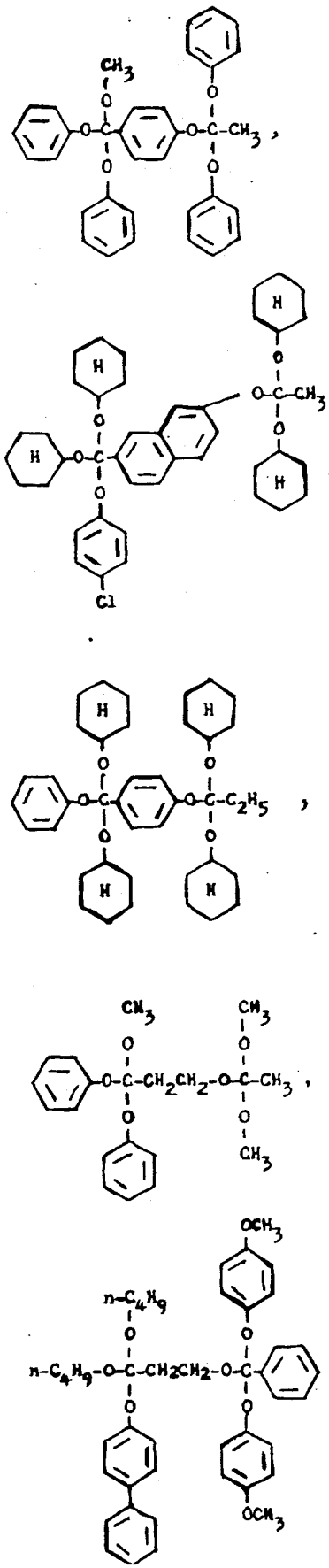
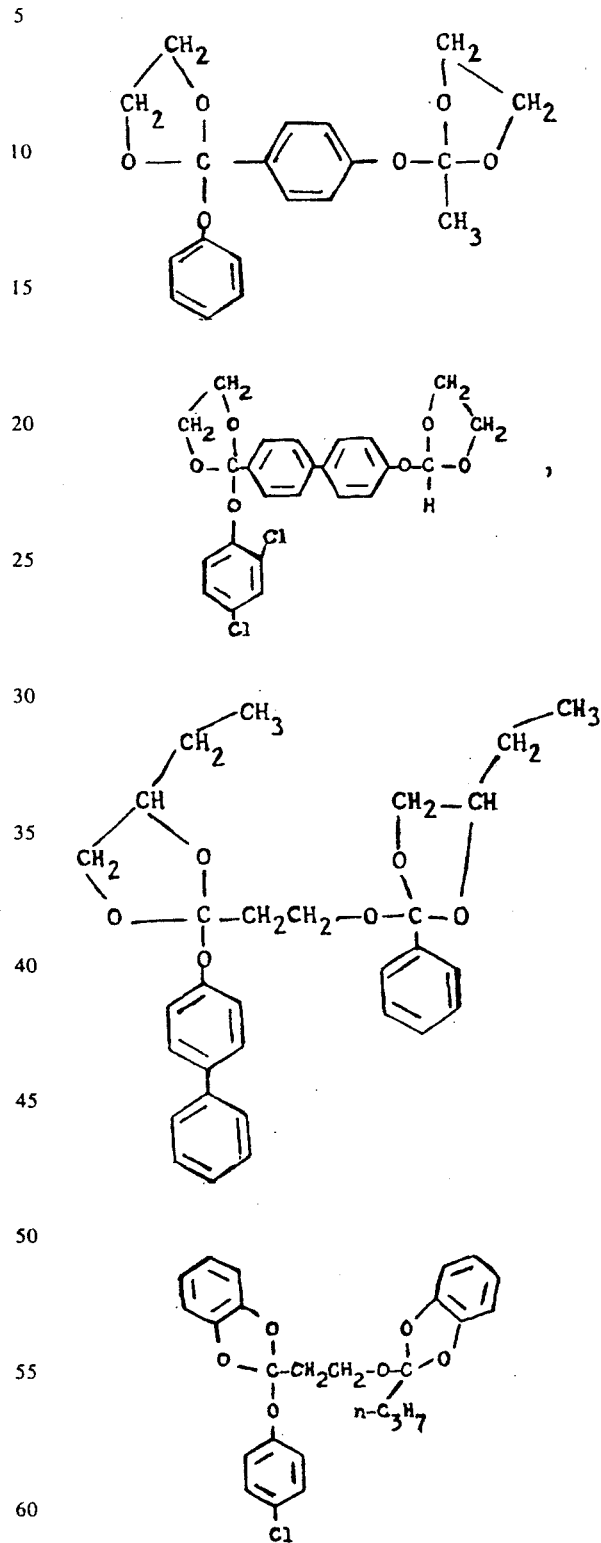
8. Compounds of the following formula (in the general formula X is a group $-Y_3-O-Z$ and Z is a group
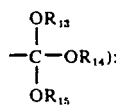

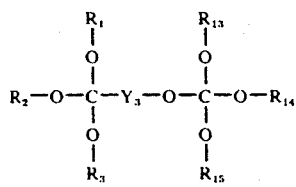
a. All of $R_1$, $R_2$, $R_3$, $R_{13}$, $R_{14}$ and $R_{15}$ are aromatic groups:
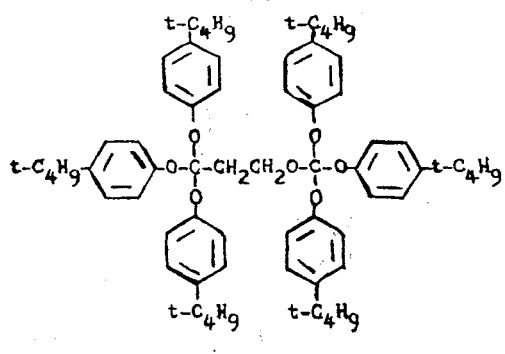
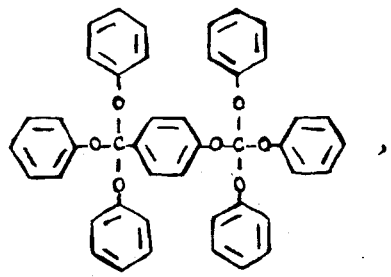,
b. One or two of $R_1$, $R_2$ and $R_3$ are aliphatic groups:
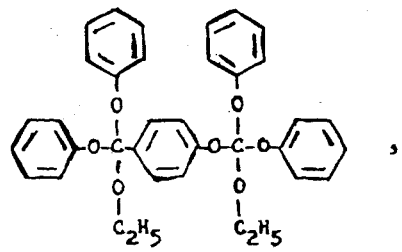,
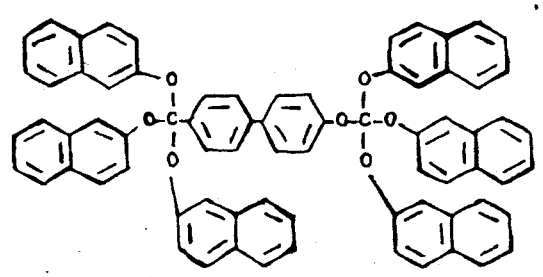,
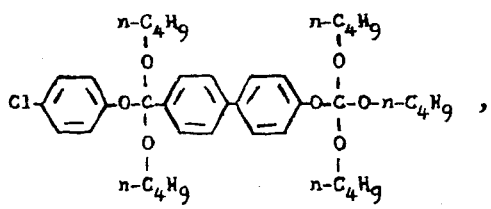,
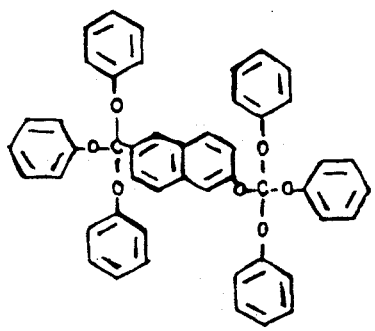,
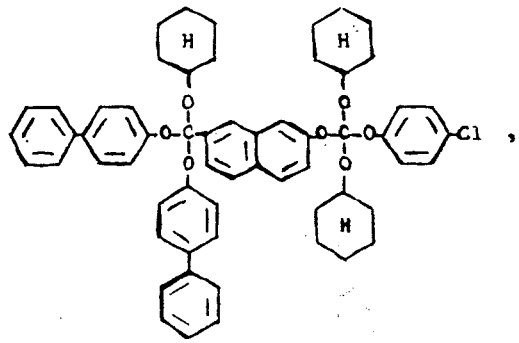,
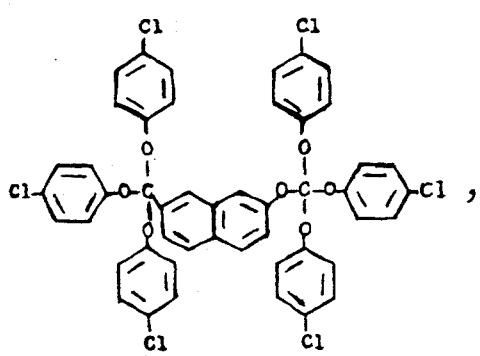,
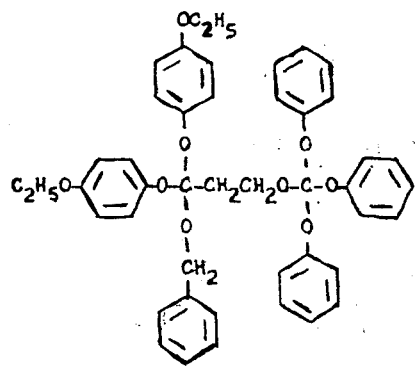

c. Two of $R_1$, $R_2$ and $R_3$ and/or two of $R_{13}$, $R_{14}$ and $R_{15}$ are bonded to form a ring:

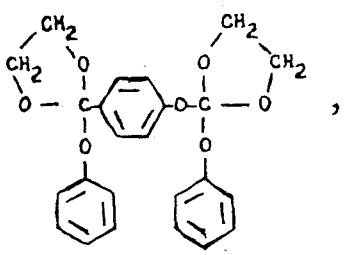

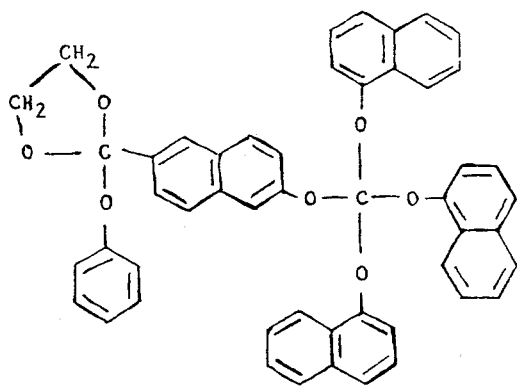

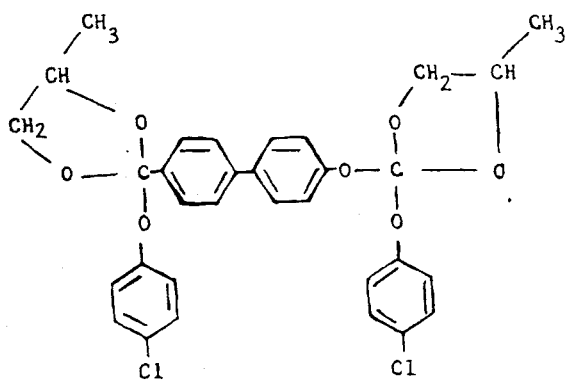

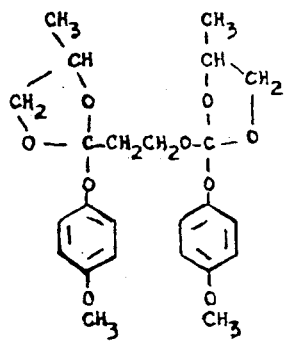

Among the above exemplified compounds, those having a greater number of ester-forming aryloxy groups in the molecule are especially effective for promoting the polycondensation reaction and reducing the terminal carboxyl group content. Optimum results are obtained by the use of promotors of this invention in which all of $R_1$ to $R_7$, $R_9$, $R_{10}$ and $R_{12}$ to $R_{15}$ in the above general formula (I) are mono-valent aromatic groups, especially phenyl and naphthyl groups, or two of these groups are bonded together to form a ring, the remaining groups being mono-valent aromatic groups, especially phenyl and naphthyl groups.

Polycondensation reaction promotors of this invention where p in the above general formula (I) is 0 (ortho-esters of oxalic acid) react with terminal carboxyl groups of polyesters and thus are decomposed and expelled from the polycondensation system. Therefore, no oxalic acid groups are introduced into resulting polyesters and in this case it is possible to obtain substantially homopolymeric polyesters.

Similar results are obtained when ortho-esters of terephthalic acid are added to polyalkylene terephthalates or when ortho-esters of 2,6-naphthalene-dicarboxylic acid are added to polyalkylene-2,6-naphthalene dicarboxylates.

The polyester obtained by the use of the polycondensation reaction promotor of this invention is characterized by a very low content of terminal carboxyl groups and diethylene glycol units and is excellent in color hue. It is also characterized in that by virtue of the low content of diethylene glycol units, the polyester possesses excellent stability against oxidation.

Still further, in this invention it is possible to greatly shorten the time required for the polycondensation reaction as compared with the conventional process, by suitably adjusting the added amount of the aromatic ortho-ester. Thus, this invention has various meritorious advantages over the prior art.

We have already invented a process for preparing polyesters of low free carboxyl group content at high polycondensation rates which comprises adding an ortho-carbonate such as tetraphenyl ortho-carbonate or di-n-butyl-diphenyl orthocarbonate to the polyester polycondensation system at the stage where the intrinsic viscosity of the polyester reaches at least 0.2 (see, for instance, our copending U.S. patent applications Ser. Nos. 124,507 and 234,643, and Dutch Patent Application Laid-Open Specification Nos. 71/03731 and 72/03605). As compared with the previous invention using the ortho-carbonate, this invention employing the aromatic ortho-ester can prevent formation of diethylene glycol units in the polyester. According to this invention, it is possible to prepare by a simple operation substantially linear polyesters having a diethylene glycol content as low as less than 1% by weight of the polyester and a free carboxyl group content as low as 4 equivalents per $10^6$ g of the polyester, by selecting suitable conditions. Moreover, according to this invention, it is possible greatly to increase the rate of the polycondensation reaction by adjusting the amount of the aromatic ortho-ester to be added within a suitable range.

Since highly polymerized polyesters prepared according to this invention exhibit a very low content of the diethylene glycol units and free carboxyl groups, they have excellent thermal stability under wet or moist conditions, are stabile against oxidative degradation, and in their other physical and chemical properties are comparable to those of polyesters prepared by conventional processes. For instance, the dyeability of fibers of polyethylene terephthalate prepared according to this invention with disperse dyes is comparable to that of fibers of polyethylene terephthalate prepared according to the conventional processes. While the thermal stability under wet or moist conditions and stability against the oxidative degradation of the polyesters prepared according to this invention are far superior to those of polyethylene terephthalate prepared by conventional processes.

In this invention, the amount of the aromatic ortho-ester to be added to the polycondensation reaction system is not particularly critical. However, it is generally preferred that the amount of the aromatic ortho-ester to be added at one time is N mole % expressed by the following formula (II), especially N' mole % expressed by the following formula (II'):

$$0.05 \times [\eta]^{-1.3} \leq N \leq 3 \times [\eta]^{-1.3} \quad (II)$$

$$0.1 \times [\eta]^{-1.3} \leq N' \leq 1 \times [\eta]^{-1.3} \quad (II')$$

wherein $[\eta]$ designates the intrinsic viscosity of the polyester at the time when the aromatic orthoester is added, and N or N' stands for the mole percent of the aromatic ortho-ester to be added based on the total acid components constituting the polyester.

By the term "amount added at one time" is not always meant an amount added in an instant but an amount added over a reasonable period of time.

As is apparent from the above formula, as the intrinsic viscosity of the polyester to which the aromatic ortho-ester is added increases the amount of the aromatic ortho-ester to be added can be reduced. Even if the aromatic ortho-ester is added in a small amount, some effect in keeping with the amount added can be obtained, and the greater the amount added, the greater is the effect of reducing the free carboxyl group content.

Where the added amount of the aromatic orthoester is suitably adjusted in the light of conditions of formula (II), especially formula (II'), there can be attained not only the effect of reducing the free carboxyl group content in the final polyester to a preferable level, but also the effect of noticeably increasing the rate of the polycondensation reaction after the addition of the aromatic ortho-ester. Furthermore, if the addition is effected at a suitable stage as mentioned above, it is possible to reduce the free carboxyl group content to such a degree as is hardly attainable or impossible in the conventional processes without formation of diethylene glycol units, for instance, to less than 15 equivalents per $10^6$ g of polyester. Moreover, it is possible to obtain easily a very highly polymerized linear polyester having an intrinsic viscosity of 0.85 or more and a diethylene glycol unit content of 1.0% by weight or less.

Preferable amounts of the aromatic ortho-ester to be added and preferable manners of the addition may be easily determined by those skilled in the art based on experimental results of the comparison of the intrinsic viscosity of the polyester at the time when the addition is effected, with the intrinsic viscosity of the polyester obtained by conducting the polycondensation for a certain period of time after the addition of the aromatic ortho-ester, in the light of conditions of formula (II) or (II').

In this invention, after the aromatic ortho-ester is added, the heating is further continued at a subatmospheric pressure while maintaining the reaction mixture in the molten state, until the free carboxyl group content of the resulting polyester reaches a desired level. This polycondensation is accomplished by heating the reaction mixture under conditions such that the reaction mixture will be maintained in the molten state at a subatmospheric pressure of less than 100 mm Hg, especially less than 50 mm Hg, and it is especially preferred that the heating reaction is carried out at subatmospheric pressure at 250° to 300°C.

After the addition of the aromatic ortho-ester, the polycondensation reaction may be conducted in the solid phase. In this case, the polymerization temperature is selected, for instance, within a range of from a temperature lower by 70°C. than the melting point of the polyester to a temperature lower by 20°C. than the melting point of the polyester. This reaction may be conducted under reduced pressure, or it may also be conducted in an inert atmosphere under reduced or elevated pressure or under atmospheric pressure.

In this invention, the aromatic ortho-ester is added to a molten polyester. In case the addition of the aromatic ortho-ester is before the intrinsic viscosity of the molten polyester reaches 0.2, the reduction of the free carboxyl group content in the final polyester is not very prominent irrespective of the amount of the aromatic ortho-ester added, as compared with the case where the aromatic ortho-ester is not added. In such case, if the amount of the aromatic ortho-ester is too large, the rate of the polymerization reaction is lowered and it is difficult to obtain a polyester having a high degree of polymerization. For these reasons, in this invention the aromatic ortho-ester is added to a molten polyester at the state where its intrinsic viscosity reaches preferably at least 0.2. Particularly good results are obtained when the aromatic ortho-ester is added to a molten polyester having an intrinsic viscosity of at least 0.3.

If the addition of the aromatic ortho-ester is effected at any stage of the polycondensation reaction after the intrinsic viscosity of a molten polyester has reached preferably at least 0.2, more preferably at least 0.3, the intended effect of reducing the free carboxyl group content in the final polyester can still be attained efficiently. In other words, there is no upper limit on the intrinsic viscosity of a polyester to which the aromatic ortho-ester is added.

Accordingly, in this invention it is possible to reduce effectively the free carboxyl group content of commercially available polyesters prepared by conventional techniques by remelting such commercially available polyester, adding the aromatic ortho-ester to the polyester melt, and further conducting the polycondensation reaction to a desired extent while maintaining the polyester in the molten state at a subatmospheric pressure. It is also effective to add an aromatic ortho-ester to a molten polyester and then conduct the polycondensation reaction in the solid phase. In these cases, the degree of polymerization of the polyester can be further heightened, as is described above, by adjusting suitably the amount of the aromatic ortho-ester to be added.

As is mentioned above, in this invention the addition of the aromatic ortho-ester may be effected at any stage after the intrinsic viscosity of the polyester has reached preferably at least 0.2, more preferably at least 0.3. If this requirement is satisfied, the addition of the aromatic ortho-ester may be all at one time or the aromatic ortho-ester may be added in divided portions at a desired frequency. It is preferable that the addition is effected all at one time when the intrinsic viscosity of the polyester to which the aromatic ortho-ester is added is about 0.1 – 0.5 lower than the intrinsic viscosity of the intended final polyester.

The process of this invention will now be illustrated by reference to Examples. In the Examples, the value of the intrinsic viscosity is calculated from the value measured at 35°C. with respect to a solution of the polyester in ortho-chlorophenol as described previously, the content of the terminal carboxyl groups is measured in accordance with the method of A. Comix [Makromol. Chem., 26, 226 (1958)], and the content of the diethylene glycol units is measured by gas chromatography in accordance with the method of Hans-Dieter and Eberhard Tucek [Faserforschung und Textiltechnik, 21, 205 (1970)].

EXAMPLES 1 to 34 and COMPARATIVE EXAMPLES 1 to 11

These Examples illustrate effects attained by addition of various aromatic ortho-ester additives.

An ester-exchange reaction vessel was charged with 97 g of dimethyl terephthalate, 69 g of ethylene glycol, 0.04 g of antimony trioxide and 0.07g of calcium acetate monohydrate, and the ester-exchange reaction was carried out at 160° – 225°C. Methanol formed as a result of the ester-exchange reaction was distilled off.

After completion of the ester-exchange reaction, phosphorous acid was added to the reaction mixture in an amount equimolar to calcium acetate. The reaction mixture was transferred into a polymerization vessel, and the inside temperature was raised to 265°C. over a period of about 30 minutes. In the subsequent 30 minutes the inside temperature was elevated to 275°C. and the inside pressure was reduced to a high vacuum of 0.1 – 0.3 mm Hg, following which the polycondensation was further conducted for 55 minutes under this high vacuum of 0.1 – 0.3 mm Hg to obtain a polyester having an intrinsic viscosity of 0.5. The inside pressure of the vessel was returned to atmospheric pressure by introduction of nitrogen, and an aromatic ortho-ester indicated in Table 1 was added to the reaction mixture in an amount of 0.5 – 1.0 mol % based on the terephthalic acid component. The reaction was carried out for 3 minutes under atmospheric pressure, following which the pressure was reduced and the polycondensation reaction was further continued for 30 – 60 minutes under a high vacuum of 0.1 – 0.3 mm Hg. The intrinsic viscosity $[\eta]$, the free carboxyl group content [COOH] (—COOH eq/$10^6$ g polymer) and the diethylene glycol unit content [DEG] (diethylene glycol % by weight based on polymer) of the resulting polyester are shown in Table 1.

For comparison, the above run was repeated by employing an aromatic ortho-ester in which $R_1$ to $R_3$ are groups having a relatively high molecular weight (Comparative Example 16–17) or by conducting the polycondensation reaction under a high vacuum of 0.1 – 0.3 mm Hg for 85 minutes without addition of any ortho-ester (Comparative Example 3). Results of determination of the intrinsic viscosity, free carboxylic group content and the diethylene glycol unit content of the resulting polyester are also indicated in Table 1.

The above run was repeated by employing alkyl ortho-esters (Comparative Examples 4 to 6), ortho-carbonates (Comparative Examples 7 to 11) and alkyl orthoesters. In these comparative runs, the polymerization rate was low, and the terminal carboxyl group content was not sufficiently low in the resulting polyesters. Especially when ortho-carbonates were employed, the amount of diethylene glycol units formed as by-products was greatly increased.

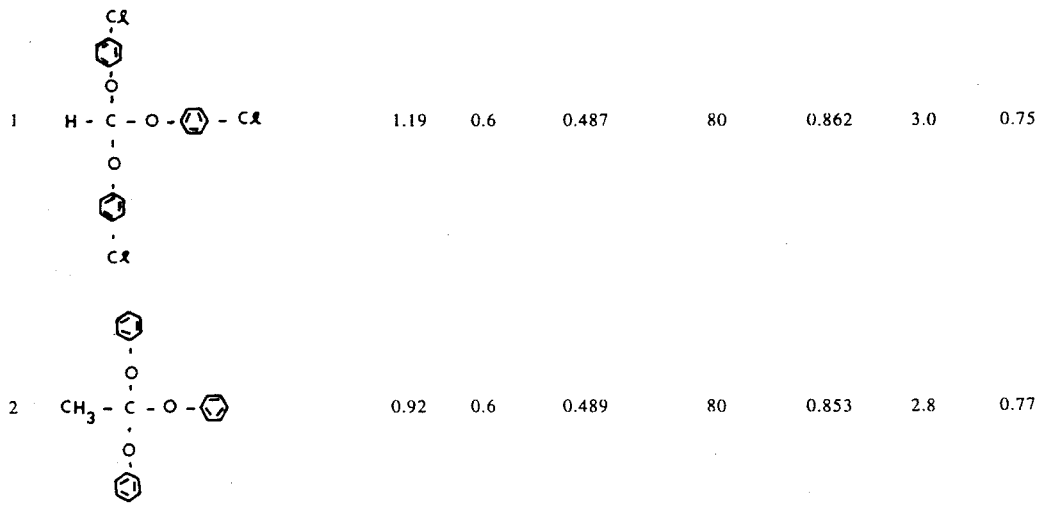

Table 1

| Example No. | Aromatic ortho-ester Kind | Amount added (g) | (mol%) | $[\eta]$ of polyester at time of addition of aromatic ortho-ester | High vacuum reaction time after addition of aromatic ortho-ester (min.) | $[\eta]$ | [COOH] | [DEG] |
|---|---|---|---|---|---|---|---|---|
| 1 | H–C(–O–⌬–Cl)(–O–⌬–Cl) with Cl substituents | 1.19 | 0.6 | 0.487 | 80 | 0.862 | 3.0 | 0.75 |
| 2 | $CH_3$–C(–O–⌬)$_3$ | 0.92 | 0.6 | 0.489 | 80 | 0.853 | 2.8 | 0.77 |

Table 1-continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | [η] | [COOH] | [DEG] |
|---|---|---|---|---|---|---|---|---|
| 3 | (structure) | 1.75 | 0.6 | 0.505 | 80 | 0.971 | 1.9 | 0.78 |
| 4 | (structure) | 1.98 | 0.6 | 0.493 | 80 | 0.983 | 2.1 | 0.78 |
| 5 | (structure) | 1.24 | 0.6 | 0.497 | 80 | 0.998 | 2.3 | 0.80 |
| 6 | (structure) | 1.47 | 0.6 | 0.507 | 80 | 0.952 | 2.2 | 0.75 |
| 7 | (structure) | 1.43 | 0.6 | 0.486 | 80 | 0.832 | 2.6 | 0.76 |
| 8 | (structure) | 2.21 | 0.6 | 0.501 | 80 | 0.867 | 2.4 | 0.80 |
| 9 | (structure) | 1.51 | 0.6 | 0.508 | 80 | 0.942 | 2.5 | 0.79 |
| 10 | (structure) | 2.02 | 0.6 | 0.479 | 80 | 0.967 | 1.9 | 0.82 |

Table 1-continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | [η] | [COOH] | [DEG] |
|---|---|---|---|---|---|---|---|---|
| 11 | (structure) | 1.92 | 0.6 | 0.491 | 80 | 0.941 | 2.1 | 0.77 |
| 12 | (structure) | 0.54 | 0.6 | 0.490 | 100 | 0.707 | 3.6 | 0.81 |
| 13 | (structure) | 0.54 | 0.6 | 0.480 | 100 | 0.703 | 3.7 | 0.80 |
| 14 | (structure) | 0.99 | 0.6 | 0.497 | 90 | 0.908 | 3.4 | 0.82 |
| 15 | (structure) | 1.60 | 0.6 | 0.503 | 80 | 0.950 | 2.2 | 0.81 |
| 16 | (structure) | 1.22 | 0.6 | 0.507 | 90 | 0.933 | 2.6 | 0.83 |
| 17 | (structure) | 1.13 | 0.6 | 0.497 | 90 | 0.948 | 2.5 | 0.79 |
| 18 | (structure) | 1.03 | 0.6 | 0.510 | 90 | 0.783 | 2.6 | 0.77 |

Table 1-continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | [η] | [COOH] | [DEG] |
|---|---|---|---|---|---|---|---|---|
| 19 | (structure) | 1.27 | 0.6 | 0.476 | 90 | 0.805 | 2.7 | 0.77 |
| 20 | (structure) | 1.12 | 0.6 | 0.521 | 90 | 0.734 | 3.0 | 0.79 |
| 21 | (structure) | 1.14 | 0.6 | 0.510 | 90 | 0.784 | 2.7 | 0.79 |
| 22 | (structure) | 1.27 | 0.6 | 0.489 | 90 | 0.801 | 2.6 | 0.81 |
| 23 | (structure) | 1.21 | 0.6 | 0.492 | 90 | 0.773 | 2.9 | 0.82 |
| 24 | (structure) | 1.36 | 0.6 | 0.499 | 100 | 0.724 | 2.9 | 0.80 |
| 25 | (structure) | 0.76 | 0.6 | 0.482 | 110 | 0.725 | 3.2 | 0.77 |

Table 1-continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | [η] | [COOH] | [DEG] |
|---|---|---|---|---|---|---|---|---|
| 26 | CH₃–C(OH)(O–Ph)(O–Ph) structure | 0.94 | 0.6 | 0.495 | 100 | 0.782 | 3.4 | 0.79 |
| 27 | bis-ortho-ester with CH₂Ph groups | 1.92 | 0.6 | 0.499 | 100 | 0.720 | 3.3 | 0.78 |
| 28 | bis-ortho-ester with C₂H₅ groups | 1.21 | 0.6 | 0.515 | 115 | 0.671 | 3.1 | 0.76 |
| 29 | CH₃O–C(CH₃)(O)(O–Ph)–CO–Ph | 0.87 | 0.6 | 0.492 | 100 | 0.683 | 3.0 | 0.77 |
| 30 | CH₃O–C(CH₃)(OPh)–Ph–N(O)–O–Ph | 1.09 | 0.6 | 0.488 | 100 | 0.676 | 3.2 | 0.79 |
| 31 | aromatic ortho-ester with H groups | 1.83 | 0.6 | 0.512 | 100 | 0.685 | 3.5 | 0.79 |
| 32 | sulfonyl-containing ortho-ester with C₂H₅ groups | 1.41 | 0.6 | 0.476 | 115 | 0.665 | 3.7 | 0.78 |

Table 1 -continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | [η] | [COOH] | [DEG] |
|---|---|---|---|---|---|---|---|---|
| 33 | (structure: bis-phenyl ortho-ester with CH₂ bridge and CH₃) | 2.13 | 0.6 | 0.479 | 115 | 0.667 | 3.8 | 0.77 |
| 34 | (structure: naphthalene bis ortho-ester with OC₂H₅ and phenyl groups) | 1.89 | 0.6 | 0.511 | 90 | 0.843 | 2.1 | 0.83 |

| Comparative Example No. | Additive Kind | Amount added (g) | (mol%) | [η] of polyester at time of addition of additive | Total time of reaction after addition of additive (min.) | Resulting Polyester [η] | [COOH] | [DEG] |
|---|---|---|---|---|---|---|---|---|
| 1 | HC(O-⟨⟩-⟨⟩-C₈H₁₇)₃ | 2.57 | 0.6 | 0.510 | 90 | 0.658 | 7.5 | 0.75 |
| 2 | ⟨⟩-C(O-⟨⟩-⟨⟩-C₈H₁₇)₃ | 2.94 | 0.6 | 0.506 | 90 | 0.642 | 7.2 | 0.77 |
| 3 | not added | — | — | — | 90 | 0.660 | 15.3 | 0.76 |
| 4 | (triethyl orthoformate derivative) | 0.45 | 0.6 | 0.497 | 85 | 0.623 | 8.7 | 0.79 |
| 5 | (bis-orthoester with (CH₂)₂ bridge, OC₂H₅ groups) | 0.97 | 0.6 | 0.501 | 85 | 0.637 | 7.2 | 0.78 |
| 6 | (phenyl tri-n-butyl orthoester) | 0.93 | 0.6 | 0.484 | 85 | 0.619 | 8.0 | 0.79 |
| 7 | (tetraphenoxy methane) | 1.15 | 0.6 | 0.499 | 80 | 0.823 | 3.6 | 0.92 |
| 8 | ″ | 1.92 | 1.0 | 0.486 | 80 | 0.956 | 2.5 | 1.30 |

Table 1-continued

| Comparative Example No. | Additive Kind | Amount added (g) | Amount added (mol%) | [η] of polyester at time of addition of additive | Total time of reaction after addition of additive (min.) | Resulting Polyester [η] | [COOH] | [DEG] |
|---|---|---|---|---|---|---|---|---|
| 9 | (C₆H₅O)₃C-OC₆H₅ (tetraphenyl orthocarbonate) | 7.69 | 4.0 | 0.500 | 80 | 0.983 | 1.9 | 1.90 |
| 10 | n-C₄H₉O-C(OnC₄H₉)(OnC₄H₉)(nC₄H₉) | 0.76 | 0.5 | 0.492 | 115 | 0.653 | 5.3 | 0.98 |
| 11 | bicyclic ortho-ester (CH₂/O\C-C/O\CH₂) | 0.66 | 1.0 | 0.495 | 85 | 0.655 | 2.1 | 1.39 |

EXAMPLE 35 to 40

These Examples illustrate the influence of the time of addition of the aromatic ortho-ester addition.

An ester-exchange reaction vessel was charged with 97 g of dimethyl terephthalate, 69 g of ethylene glycol, 0.04 g of antimony trioxide and 0.07 g of calcium acetate monohydrate, and the mixture was heated at 160° – 225°C. while methanol formed as a result of the ester-exchange reaction was distilled off.

After completing of the ester-exchange reaction, phosphorous acid was added to the reaction mixture in an amount equimolar to calcium acetate, and the reaction mixture was transferred into a polymerization vessel. The inside temperature of the vessel was raised to 265°C. over a period of about 30 minutes, and in the subsequent 30 minutes the inside temperature was elevated to 275°C. and the pressure was reduced to a high vacuum of 0.1 – 0.3 mm Hg. The reaction under this high vacuum of 0.1 – 0.3 mm Hg was carried out for a period indicated in Table 2 and the pressure was returned to atmospheric by the introduction of nitrogen. Then, an aromatic ortho-ester indicated in Table 2 was added to the reaction mixture and the reaction was carried out under atmospheric pressure for 3 minutes, following which the pressure was reduced and the polycondensation was continued under a high vacuum of 0.1 – 0.3 mm Hg. The intrinsic viscosity and free carboxyl group content of the resulting polyester are shown in Table 2.

Table 2

| Example No. | Aromatic ortho-ester Kind | Amount added (g) | Amount added (mol%) | [η] of polyester at time of addition of aromatic ortho-ester | High vacuum reaction time (min.) Before addition of aromatic ortho-ester | High vacuum reaction time (min.) After addition of aromatic ortho-ester | Resulting Polyester [η] | [COOH] | [DEG] |
|---|---|---|---|---|---|---|---|---|---|
| 35 | hexaphenyl orthocarbonate structure | 1.67 | 0.6 | 0.253 | 25 | 85 | 0.896 | 7.8 | 0.77 |
| 36 | " | " | 0.6 | 0.425 | 35 | 35 | 0.923 | 3.7 | 0.78 |
| 4 | " | " | 0.6 | 0.493 | 55 | 30 | 0.983 | 2.1 | 0.78 |
| 37 | " | " | 0.6 | 0.754 | 90 | 20 | 0.936 | 1.9 | 0.77 |

Table 2 -continued

| Example No. | Aromatic ortho-ester Kind | Amount added (g) | Amount added (mol%) | [η] of polyester at time of addition of aromatic ortho-ester | High vacuum reaction time (min.) Before addition of aromatic ortho-ester | High vacuum reaction time (min.) After addition of aromatic ortho-ester | Resulting Polyester [η] | Resulting Polyester [COOH] | Resulting Polyester [DEG] |
|---|---|---|---|---|---|---|---|---|---|
| 38 | CH₃–C(–O–Ph)₃ (triphenyl orthoacetate) | 0.92 | 0.6 | 0.251 | 25 | 80 | 0.792 | 9.9 | 0.76 |
| 39 | " | 0.92 | 0.6 | 0.426 | 35 | 35 | 0.824 | 3.9 | 0.79 |
| 2 | " | 0.92 | 0.6 | 0.489 | 55 | 25 | 0.853 | 2.8 | 0.77 |
| 40 | " | 0.92 | 0.6 | 0.749 | 90 | 10 | 0.879 | 2.5 | 0.76 |

EXAMPLES 41 to 46

These Examples illustrate the influences of the amount of the aromatic ortho-ester added.

An ester-exchange reaction vessel was charged with 97 g of dimethyl terephthalate, 69 g of ethylene glycol, 0.04 g of antimony trioxide and 0.07 g of calcium acetate monohydrate, and the reactants were heated at 160° – 225°C. while methanol formed as a result of the ester-exchange reaction was distilled off.

After completion of the ester-exchange reaction, phosphorous acid was added to the reaction mixture in an amount equimolar to calcium acetate, and the reaction mixture was transferred into a polymerization vessel. The inside temperature of the vessel was raised to 265°C. over a period of about 30 minutes, and in the subsequent 30 minutes the inside temperature was elevated to 275°C. and the pressure was reduced to a high vacuum of 0.1 – 0.3 mm Hg, following which the high vacuum reaction was conducted for 60 minutes to obtain a polyester having an intrinsic viscosity of about 0.6. At this point the pressure was returned to atmospheric by the introduction of nitrogen. Hexaphenyl ortho-terephthalate was added to the reaction mixture in an amount indicated in Table 3, and the reaction was carried out under atmospheric pressure for 3 minutes, following which the pressure was reduced again and the polycondensation was continued for 30 minutes under a high vacuum of 0.1 – 0.3 mm Hg. The intrinsic viscosity, the terminal free carboxyl group content and the diethylene glycol unit content of the resulting polyester are shown in Table 3.

Table 3

| Example No. | Aromatic ortho-ester Kind | Amount added (g) | Amount added (mol%) | [η] of polyester at time of addition of aromatic ortho-ester | High vacuum reaction time after addition of aromatic ortho-ester (min.) | Resulting polyester [η] | Resulting polyester [COOH] | Resulting polyester [DEG] |
|---|---|---|---|---|---|---|---|---|
| 41 | hexaphenyl ortho-terephthalate | 0.99 | 0.3 | 0.590 | 90 | 0.892 | 9.8 | 0.77 |
| 42 | " | 3.29 | 1.0 | 0.585 | 90 | 0.964 | 3.0 | 0.79 |
| 43 | " | 13.18 | 4.0 | 0.594 | 90 | 0.921 | 3.0 | 0.83 |
| 44 | (cyclic aromatic ortho-ester) | 0.61 | 0.3 | 0.512 | 90 | 0.862 | 3.4 | 0.79 |

Table 3-continued

| Example No. | Aromatic ortho-ester Kind | Amount added (g) | (mol%) | [η] of polyester at time of addition of aromatic ortho-ester | High vacuum reaction time after addition of aromatic ortho-ester (min.) | Resulting polyester [η] | [COOH] | [DEG] |
| --- | --- | --- | --- | --- | --- | --- | --- | --- |
| 16 | (structure) | 1.22 | 0.6 | 0.507 | 90 | 0.933 | 2.6 | 0.82 |
| 45 | " | 2.03 | 1.0 | 0.508 | 90 | 0.930 | 2.4 | 0.83 |
| 46 | " | 8.13 | 4.0 | 0.504 | 90 | 0.905 | 2.1 | 0.86 |

EXAMPLES 47 to 49 and COMPARATIVE EXAMPLE 12

These Examples illustrate the preparation of polyethylene-2,6-naphthalate.

An ester-exchange reaction vessel was charged with 122 g of dimethyl naphthalene-2,6-dicarboxylate, 69 g of ethylene glycol, 0.02 g of antimony trioxide and 0.07 g of calcium acetate monohydrate, and the reactants were heated at 160° – 225°C. while methanol formed as a result of the ester-exchange reaction was distilled off.

After completion of the ester-exchange reaction, phosphorous acid was added to the reaction mixture in an amount equimolar to calcium acetate. The reaction mixture was transferred into a polymerization vessel, and the inside temperature of the vessel was raised to 265°C. over a period of about 30 minutes. In the subsequent 30 minutes, the inside temperature was elevated to 285°C. and the inside pressure was reduced to a high vacuum of 0.1 – 0.3 mm Hg, following which the polycondensation was carried out for 50 minutes under this high vacuum of 0.1 – 0.3 mm Hg to obtain a polyester having an intrinsic viscosity of about 0.50. At this point the inside pressure was returned to atmospheric by the introduction of nitrogen, and an aromatic ortho-ester indicated in Table 4 was added to the reaction mixture in an amount of 1.0 mole % based on the naphthalene-2,6-dicarboxylic acid component. The reaction was carried out under atmospheric pressure for 3 minutes, following which the pressure was reduced again and the polycondensation was conducted under a high vacuum of 0.1 – 0.3 mm Hg for 30 minutes. The intrinsic viscosity [η], the terminal free carboxyl group content and the diethylene glycol content of the resulting polyester are shown in Table 4.

For comparison, the high vacuum polycondensation was carried out under 0.1 – 0.3 mm Hg for 55 minutes, and sampling was conducted. At this point, the sampled polyester had an intrinsic viscosity of 0.55 and a terminal free carboxyl group content of 14 eq/$10^6$ g polyester. This polymer was further subjected to the polycondensation reaction under high vacuum for 30 minutes. Results are also shown in Table 4.

Table 4

| Example No. | Aromatic ortho-ester Kind | Amount added (g) | (mol%) | [η] of polyester at time of addition of aromatic ortho-ester (min.) | Resulting polyester [η] | [COOH] | [DEG] |
| --- | --- | --- | --- | --- | --- | --- | --- |
| 47 | (structure) | 3.54 | 1.0 | 0.510 | 0.784 | 2.7 | 0.70 |
| 48 | (structure) | 3.26 | 1.0 | 0.511 | 0.740 | 2.8 | 0.71 |

Table 4

| Example No. | Aromatic ortho-ester Kind | Amount added (g) | Amount added (mol%) | $[\eta]$ of polyester at time of addition of aromatic ortho-ester (min.) | Resulting polyester $[\eta]$ | [COOH] | [DEG] |
|---|---|---|---|---|---|---|---|
| 49 | (tetraphenyl orthoester structure) | 2.06 | 1.0 | 0.498 | 0.790 | 2.4 | 0.69 |
| Comp. Ex. 12 | not added (blank) | — | — | — | 0.55 / 0.620 | 14.0 / 18.2 | 0.68 |

EXAMPLES 50 to 52 and COMPARATIVE EXAMPLE 13

These examples illustrate embodiments where tetramethylene glycol is used as the glycol component.

An ester-exchange reaction vessel was charged with 97 g of dimethyl terephthalate, 100 g of tetramethylene glycol and 0.04 g of tetrabutyl titanate, and the reactants were heated at 170° – 230°C. to effect the ester-exchange reaction. After completion of the ester-exchange reaction, 0.036 g of trimethyl phosphate was added to the reaction mixture, and it was transferred into a polymerization vessel. The inside temperature was raised to 250°C. over a period of about 30 minutes and the pressure was reduced to 30 mm Hg. In the subsequent 30 minutes, the pressure was further reduced to a high vacuum of 0.1 – 0.2 mm Hg, following which the polycondensation was further continued under a high vacuum of 0.1 – 0.2 mm Hg for 25 minutes.

The intrinsic viscosity of the resulting polyester was about 0.5. At this point the pressure was returned to atmospheric by the introduction of nitrogen, and an aromatic ortho-ester indicated in Table 5 was added to the reaction mixture (the value of the mole % being one based on the acid component of the polyester). Then, the reaction was carried out under atmospheric pressure for 5 minutes, and the pressure was reduced. Under a high vacuum of 0.1 – 0.2 mm Hg the polycondensation was conducted for 20 – 50 minutes. The intrinsic viscosity $[\eta]$, the free carboxyl content and the ditetramethylene glycol content of the resulting polyester are shown in Table 5.

For comparison, the high vacuum polycondensation was carried out under 0.1 – 0.3 mm Hg for 60 minutes without addition of any ortho-ester and sampling was conducted. At this point, the sampled polyester had an intrinsic viscosity of 0.75, and a terminal carboxyl group content of 12.2 eq/$10^6$ g polyester and a ditetramethylene glycol content of 0.48 wt%. This polyester was subjected to the polycondensation reaction under high vacuum for 60 minutes. (Comparative Example 13). The results of this comparative run are also shown in Table 5.

Table 5

| Example No. | Aromatic ortho-ester Kind | Amount added (g) | Amount added (mol%) | $[\eta]$ of polyester at time of addition of aromatic ortho-ester | High vacuum reaction time after addition of aromatic ortho-ester | Resulting polyester $[\eta]$ | [COOH] | [Tetramethylene glycol] |
|---|---|---|---|---|---|---|---|---|
| 50 | (structure) | 3.29 | 1.0 | 0.503 | 60 | 1.20 | 3.2 | 0.51 |
| 51 | (structure) | 2.44 | 1.0 | 0.512 | 60 | 1.13 | 3.1 | 0.49 |
| 52 | (structure with $C_2H_5$ groups) | 2.33 | 1.0 | 0.508 | 60 | 0.95 | 4.4 | 0.50 |
| Comp. Ex. 13 | not added (Blank) | | | | (60) / (120) | 0.75 / 1.07 | 12.2 / 14.5 | 0.48 |

EXAMPLE 53 and COMPARATIVE EXAMPLE 14

These Examples illustrate embodiments where aliphatic polyesters are prepared.

A mixture of 87 g of dimethyl adipate, 118 g of hexamethylene glycol and 0.04 g of tetrabutyl titanate was heated at 170° – 220°C. to effect the ester-exchange reaction. Then, the temperature of a bath was maintained at 270°C. and the pressure was gradually reduced. Under 0.1 mm Hg the polycondensation was conducted for 60 minutes to obtain a polyester having an intrinsic viscosity of 0.48. The pressure was returned to atmospheric pressure and 2.169 g (0.6 mol%) of Hexa p-cresyl-ortho adipate was added to the reaction mixture. The pressure was reduced again and the polymerization was carried out for 30 minutes. The intrinsic viscosity and the free carboxyl group content of the resulting polyester are shown in Table 6.

For comparison, the polymerization was carried out similarly under 0.1 mm Hg for 90 minutes without addition of hexa p-cresyl-ortho adipate (Comparative Example 14), results of which are also shown in Table 6.

the pressure was gradually reduced. The polymerization was carried out under a reduced pressure of 0.2 mm Hg for 600 minutes. The intrinsic viscosity of the resulting polyester was 0.420. At this point 1.79 g (0.6 mol%) of diphenyl p-(triphenoxy)methylphenyl ortho acetate was added to the reaction mixture, and the polymerization was further conducted under 0.2 mm Hg for 60 minutes. The resulting polyester had an intrinsic viscosity of 0.501 and a free carboxyl group content of 2.1 eq/$10^6$ g polyester.

For comparison, the polymerization was carried out under 0.1 mm Hg without employing any aromatic orthoester for 660 minutes. The resulting polyester had an intrinsic viscosity of 0.453 and a free carboxyl group content of 10.3 eq/$10^6$ g polyester.

EXAMPLES 55, 56 and COMPARATIVE EXAMPLE 15

These Examples illustrate the preparation of copolyesters.

An ester-exchange reaction vessel was charged with mixture in an amount of 1.0 mole % based on the acid component of the polyester. The reaction was carried

Table 6

| Example No. | Total time of high vacuum reaction (minutes) | Resulting polyester [η] | Fee —COOH content | Diethylene glycol content |
|---|---|---|---|---|
| Example 53 | 90 | 0.84 | 6.4 | 0.81 |
| Comparative Example 14 | 90 | 0.71 | 19.0 | 0.80 |

EXAMPLE 54 and COMPARATIVE EXAMPLE 15

These Examples illustrate the preparation of polyester from a hydroxycarboxylic acid.

A mixture of 98 g of methyl β-hydroxyethoxybenzoate, 34 g of ethylene glycol and 0.02 g of tetraisopropyl titanate was heated at 160° – 225°C. to effect the ester-exchange reaction. Methanol formed as a result of the ester-exchange reaction was distilled off. Then, the temperature of a bath was maintained at 285°C. and out for 5 minutes under atmospheric pressure, and the pressure was reduced again and the polymerization was conducted under 0.1 – 0.2 mm Hg for 50 minutes. The intrinsic viscosity [η] and the terminal carboxyl group content (—COOH eq/$10^6$ g polyester) are shown in Table 7.

For comparison, the polymerization was conducted under 0.1 – 0.3 mm Hg for 90 minutes without employing any aromatic ortho-ester (Comparative Example 15). Results of this comparative run are also shown in Table 7.

Table 7

| Example No. | Aromatic ortho-ester Kind | Amount added (g) | (mol%) | [η] of polyester at time of addition of aromatic ortho-ester | High vacuum reaction time of after addition of aromatic ortho-ester | Resulting Polyester [η] | [COOH] | [DEG] |
|---|---|---|---|---|---|---|---|---|
| 55 | 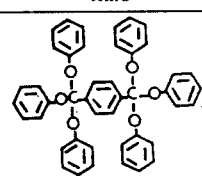 | 1.98 | 0.6 | 0.413 | 90 | 0.846 | 3.3 | 0.79 |
| 56 | 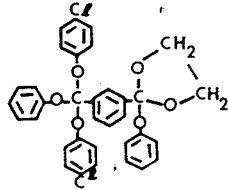 | 1.80 | 0.6 | 0.405 | 90 | 0.798 | 3.0 | 0.80 |
| Comparative Example 15 | not added | — | — | — | (90) | 0.662 | 17.3 | 0.77 |

88.2 g of dimethyl terephthalate, 8.8 g (10 mole %) of dimethyl isophthalate, 69 g of ethylene glycol, 0.07 g of magnesium acetate, 0.004 g of cobalt acetate and 0.04 g of antimony trioxide, and the reactants were heated at 170° – 230°C. to effect the ester-exchange reaction. After completion of the ester-exchange reaction, trimethyl phosphate was added to the reaction mixture in an amount equimolar to the sum of magnesium acetate and cobalt acetate. Then, the reaction mixture was transferred into a polymerization vessel, and the inside temperature of the vessel was raised to 260°C. over a period of about 30 minutes and the pressure was reduced to 30 minutes. In the subsequent 30 minutes, the inside temperature was elevated to 285°C. and the pressure was reduced to a high vacuum of 0.1 – 0.2 mm Hg, following which the polymerization was continued for 40 minutes under 0.1 – 0.2 mm Hg. The resulting polyester had an intrinsic viscosity of about 0.40. At this point the pressure was returned to atmospheric by the introduction of nitrogen, and an aromatic ortho-ester indicated in Table 7 was added to the reaction EXAMPLE 57 and COMPARATIVE EXAMPLE 16

These Examples illustrate the preparation of polyethylene terephthalate by the ethylene oxide process.

An autoclave equipped with a condenser was charged with 8.3 kg of terephthalic acid, 43 kg of benzene, 4.4 kg of ethylene oxide and 50 g of triethyl amine, and the reactants were reacted at 180°C. for 10 minutes in a nitrogen atmosphere. A valve disposed at the upper portion of the condenser was opened to effect the evaporation and to cool the reaction mixture to 130°C. Then, the reaction mixture was transferred into a pressure filter and unreacted terephthalic acid was removed by filtration.

At 130°C. the reaction mixture was separated into a molten phase insoluble in benzene and a benzene phase. The benzene phase was cooled to precipitate bis-$\beta$-hydroxyethyl terephthalate, the yield of which was 10.4 kg.

A polymerization vessel was charged with 19.65 kg of bis-$\beta$-hydroxyethyl terephthalate prepared by the above method, 6.06 g of antimony trioxide and 0.93 g of trimethyl phosphate, and they were reacted under atmospheric pressure at 285°C. for 15 minutes in a nitrogen current, following which the pressure was reduced to 0.5 mm Hg over a period of 45 minutes and the polymerization was carried out for 100 minutes under a reduced pressure of 0.5 – 0.2 mm Hg. At this point, the polyester exhibited an intrinsic viscosity of 0.650. Then, 236 g (0.8 mol%) of solid tri-p-meihoxyphenyl ortho-formate was added to the polyester under the above high vacuum and the polymerization was further continued for 60 minutes. The resulting polyester had an intrinsic viscosity of 0.82 and a terminal carboxyl group content of 4.6 eq/$10^6$ g polyester and diethylene glycol content of 0.66 wt% of polyester.

For comparison, the high vacuum polymerization was conducted for 160 minutes without addition of tri-p-methoxy phenyl ortho-formate. The resulting polyester had an intrinsic viscosity of 0.782 and a terminal hydroxyl group of 27.8 eq/$10^6$ g polyester and diethylene glycol content of 0.65% of polyester.

EXAMPLE 58 and COMPARATIVE EXAMPLE 17

These Examples illustrate the preparation of polyethylene terephthalate by the direct polymerization process.

An esterification vessel was charged with 83 g of terephthalic acid, 69 g of ethylene glycol, 0.04 g of antimony trioxide and 0.07 g of calcium acetate monohydrate, and they were reacted at 240°C. under pressure while water formed as a result of the reaction was distilled off.

After completion of the esterification reaction, phosphoric acid was added to the reaction mixture in an amount of 1.1 moles per mole of calcium acetate, and the reaction mixture was transferred into a polymerization vessel. Over a period of about 30 minutes, the inside temperature of the vessel was raised to 260°C. and the pressure was reduced to 30 mm Hg. In the subsequent 30 minutes, the inside temperature was elevated to 285°C. and the pressure was reduced to a high vacuum of 0.1 – 0.2 mm Hg, following which the polymerization was further conducted under 0.1 – 0.2 mm Hg for 40 minutes to obtain a polyester having an intrinsic viscosity of 0.410. At this point the pressure was returned to atmospheric by the introduction of nitrogen, and phenyl ethylene-orthobenzoate

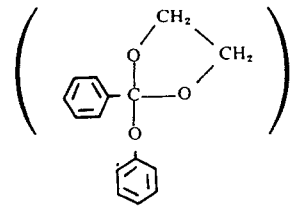

was added to the reaction mixture in an amount of 1.21 g (0.8 mole % based on the terephthalic acid component of the polyester). Then, the pressure was reduced again, and the polymerization was carried out under 0.1 – 0.2 mm Hg for 50 minutes.

The resulting polyester had an intrinsic viscosity of 0.711 and a terminal carboxyl group content of 4.2 eq/$10^6$ g polyester and diethylene glycol content of 1.43 wt% of polyester For comparison, the same procedures as above were repeated except that addition of the aromatic ortho-ester was not effected. The polymerization under high vacuum was conducted for 90 minutes. The resulting polyester had an intrinsic viscosity of 0.658 and a terminal carboxyl group content of 18.5 eq/$10^6$ g polyester and diethylene glycol of 1.43 wt% of polyester.

EXAMPLE 59 and COMPARATIVE EXAMPLE 18

These Examples illustrate the two-staged addition of the aromatic ortho-ester.

An esterification vessel was charged with 20 kg of dimethyl terephthalate, 13.2 kg of ethylene glycol, 7.4 g of manganese acetate and 8.08 g of antimony trioxide, and heated at 170°–230°C. to effect the esterexchange reaction. After completion of the ester-exchange reaction, trimethyl phosphate was added to the reaction mixture in an amount equimolar to the manganese acetate and the reaction mixture was transferred into a polymerization vessel. The inside temperature of the vessel was raised to 260°C. over a period of about 15 minutes, and in the subsequent 60 minutes, the inside temperature was elevated to 285°C. and the pressure was reduced to 0.1–0.2 mm Hg, following which the polymerization was carried out for 90 minutes under 0.1 – 0.2 mm Hg to obtain a polyester having an intrinsic viscosity of 0.525. At this point, the pressure was returned to atmospheric by the introduction of nitrogen and 151g (0.3 mol%) p-triphenoxymethyl phenylbenzoate was added to the reaction mixture. The reaction was carried out for 5 minutes under reduced pressure and the pressure was reduced again, following which the polymerization was carried out for 20 minutes under 0.1 – 0.2 mm Hg. The polyester exhibited an intrinsic viscosity of 0.732 at this point. Then, 151g (0.3 mol%) of p-triphenoxymethyl phenyl benzoate was added to the reaction mixture in the same manner as above, and the polymerization was further conducted under a high vacuum of 0.1 – 0.2 mm Hg for 45 minutes to obtain a polyester having an intrinsic viscosity of 0.993 a terminal carboxyl group content of 42 eq/$10^6$ g polyester and diethylene glycol content of 0.84 wt% of polyester.

The polyester polymer was then spun by employing a melt-spinning apparatus. The resulting filamentary yarn had an intrinsic viscosity of 0.952 and a terminal carboxyl group content of 10.3 eq/$10^6$ g polyester. The yarn was stretched at a draw ratio of 4.8 at 90°C. and at draw ratio of 1.2 at 180°C., and then subjected to the post-heat-treatment.

The resulting yarn was twisted by conventional method and formed into a tire-reinforcing cord whose heat stability under wet conditions was determined by the following method.

The sample was allowed to stand at a temperature of 25°C. and a relative humidity of 65% for 48 hours, and maintained at 150°C. for a subsequent 48 hours in the sealed state. The strength retention (%) was calculated by the following formula:

$$\text{Strength reaction (\%)} = \frac{\text{Strength (kg/2000 de) of tire cord after wet-heat resistance test}}{\text{Strength (kg/2000 de) of tire cord before wet-heat resistance test}} \times 100$$

Results are shown in Table 8.

For comparison, the high vacuum reaction was similarly conducted for 160 minutes without addition of the aromatic ortho-ester to obtain a polyester having an intrinsic viscosity of 0.80 and a terminal carboxyl group content of 25.8 eq/$10^6$ g polyester, following which the polymerization was further continued for 200 minutes under reduced pressure. The resulting highly polymerized polyethylene terephthalate having an intrinsic viscosity of 0.970, a terminal carboxyl group content of 32.0 eq/$10^6$ g polyester and diethylene glycol content of 0.83 wt% of polyester was spun, stretched and formed into a tire cord in the same manner as above. The heat stability under the wet conditions was also tested with respect to the resulting tire cord in the same manner as above. Results are shown in Table 8.

Table 8

|  | Example 59 | Comparative Example 18 |
|---|---|---|
| Intrinsic viscosity [η] of tire cord | 0.952 | 0.930 |
| Terminal —COOH content of tire cord (eq/$10^6$ g polyester | 10.3 | 39.0 |
| Strength of tire cord before wet-heat resistance test (kg/2000 de) | 14.9 | 14.7 |
| Strength retention (%) | 92 | 60 |

EXAMPLE 60

Polyester chips obtained in Examples 1, 4, 5, 6 and 30 and comparative polyester chips obtained in Comparative Examples 7, 8, 9, 10 and 11 were ground and sieved. Then, 10.00 g of the polymer having a size of 32 to 40 mesh was precisely measured and charged in a glass vessel having a diameter of 35 mm and a depth of 60 mm, and the polymer was thermally degraded in a gear oven in a hot air current at 220°C. With respect to each of the polymers, the weight decrease ratio was determined after 10 days and after 20 days, respectively, to obtain results shown in Table 9.

From these results, it will readily be understood that the weight decrease is especially great when the amount of the ortho-ester is great and the polyester has a large diethylene glycol content.

These polyesters were dried in the air at 140°C. for 4 hours and at 180°C. for another 4 hours, following which the spinning, drawing and heat treatment were carried out under the same conditions as described in Example 59.

The resulting polyethylene terephthalate filamentary yarns were wound on stainless steel yarn frames having a length of 25 cm and were thermally degraded at 200°C. for 100 hours in a gear oven. Data of the strength retention ratios are shown in Table 10.

Table 9

| Example No. | Diethylene glycol content (% by weight) | Weight Decrease (% by weight) | |
|---|---|---|---|
| | | After 10 days | After 20 days |
| 1 | 0.75 | 5.5 | 10.0 |
| 4 | 0.78 | 5.6 | 11.0 |
| 5 | 0.80 | 5.9 | 11.0 |
| 16 | 0.82 | 5.9 | 11.5 |
| 30 | 0.79 | 5.6 | 10.9 |
| Comparative Example No. | | | |
| 7 | 0.92 | 6.0 | 12.4 |
| 8 | 1.30 | 7.5 | 13.8 |
| 9 | 1.90 | 9.4 | 17.4 |
| 10 | 0.98 | 6.9 | 12.7 |
| 11 | 1.39 | 8.9 | 15.0 |

Table 10

| Example No. | Strength Retention Ratio (%) |
|---|---|
| 1 | 67.5 |
| 4 | 66 |
| 5 | 66 |
| 16 | 66.5 |
| 30 | 66 |
| Comparative Example No. | |
| 7 | 63 |
| 8 | 60 |
| 9 | 54 |
| 10 | 62.5 |
| 11 | 60 |

EXAMPLE 61 and COMPARATIVE EXAMPLE 19

An ester-exchange reaction vessel was charged with 97 g of dimethyl terephthalate, 69 g of ethylene glycol, 0.04 g of antimony trioxide and 0.07 g of calcium acetate monohydrate. The mixture was heated at 160°–225°C. and methanol formed as a result of the ester-exchange reaction was distilled off.

After completion of the ester-exchange reaction, phosphorous acid was added to the reaction mixture in an amount equimolar to the calcium acetate, and the reaction mixture was transferred to a polymerization vessel. The inside temperature was raised to 265°C. over a period of about 30 minutes, and in the subsequent 30 minutes, the inside temperature was elevated to 275°C. and the pressure was reduced to a high vacuum of 0.1 – 0.3 mm Hg. Under these temperature and pressure conditions the high vacuum reaction was conducted for about 50 minutes to form a polyester having an intrinsic viscosity of about 0.5. At this stage, the pressure of the reaction system was returned to atmospheric by the introduction of nitrogen and 1.24g (0.6 mol%) of phenyl triphenoxy-acetate was added to the reaction mixture. The reaction was carried out for 3 minutes at atmospheric pressure and then the pressure was reduced to 0.1 – 0.3 mm Hg again, under which the polycondensation was conducted for 10 minutes. The intrinsic viscosity [$\eta$] of the resulting polyester was 0.693 and the terminal carboxyl group content of the resulting polyester was 6.4 equivalents per $10^6$ g of polymer.

This polyester was solidified and ground to a size less than 10 mesh. Then, the ground polyester was dried at 160°C. for 4 hours and was polymerized in the solid phase at 230°C. for 5 hours in vacuo. The intrinsic viscosity, as calculated from the value measured in a mixed solvent of phenol and tetrachloroethane at a weight ratio of 6 : 4 at 35°C., of the resulting polyester was 0.994 and the terminal carboxyl group content was 1.0 equivalent per $10^6$ g of the polyester.

For comparison, a polyester (having an intrinsic viscosity of 0.660 and a terminal carboxyl group content of 12.0 equivalents per $10^6$ g of the polyester) prepared by continuing the high vacuum polycondensation reaction for 80 minutes without addition of the aromatic orthoester was subjected to the solid phase polymerization in the same manner as above. The resulting polyester had an intrinsic viscosity of 0.920 as calculated from the value measured in a mixed solvent of phenyl and tetrachloroethane at a weight ratio of 6 : 4 at 35°C. and a terminal carboxyl group content of 7.9 equivalents per $10^6$ g of the polyester.

What we claim is:

1. In the process for the preparation of substantially linear, highly polymerized carboxylic acid esters by removing the glycol from a glycol ester of a dicarboxylic or hydroxycarboxylic acid or its low condensate to thereby effect the polycondensation, the improvement comprising adding, as a polycondensation promoter, at least one aromatic ortho-ester expressed by the formula

  (1)

wherein X is a group —R,

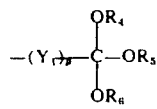

or —$(Y_2)_{\overline{p}}$ COOR$_7$ R stands for a hydrogen atom or a mono-valent organic group being inert to an ester-forming component and having a molecular weight not exceeding 250; $R_1, R_2, R_3, R_4, R_5, R_6$ and $R^7$, which may be the same or different, stand for a mono-valent organic group being inert to an ester-forming component and having a molecular weight not exceeding 250; at least one of $R_1, R_2, R_3, R_4, R_5$ and $R_6$ stand for a monovalent aromatic group; in case the ortho-ester expressed by the above formula contains R and $R_7$, at least one of $R_1, R_2$ and $R_3$ is a mono-valent aromatic group; two of $R_1, R_2$ and $R^3$ and two of $R_4, R_5$ and $R_6$ may be bonded together to form a ring; $Y_1$ and $Y_2$, which may be the same or different, stand for a divalent organic radical insert to an ester-forming component; and $p$ is 0 or 1 to a molten polyester having an intrinsic viscosity of at least 0.2, as calculated from the value measured in orthochlorophenol at 35°C., and conducting the polycondensation under conditions such that the reaction mixture is maintained in the molten or solid state.

2. The improvement according to claim 1, wherein the glycol is a 1,2-glycol or 1,4-glycol.

3. The improvement according to claim 1, wherein the dicarboxylic acid is selected from terephthalic acid and naphthalene-2,6-dicarboxylic acid.

4. The improvement according to claim 1, wherein $R_1$ to $R_7$ stand for a mono-valent aromatic group.

5. The improvement according to claim 1, wherein p is 1 and $Y_1$ and $Y_2$ is p-phenylene or 2,6-naphthalene.

6. The improvement according to claim 1, wherein $R_1$ to R7 is a phenyl or naphthyl group.

7. The improvement according to claim 1, wherein the amount of the aromatic ortho-ester to be added at one time is N mole % expressed by the following formula $$0.05 \times [\eta]^{-1.3} \leq N \leq 3 \times [\eta]^{-1.3}$$

wherein [$\eta$] designates the intrinsic viscosity, as calculated from the value measured in orthochlorophenol at 35°C., of the polyester at the time when the aromatic ortho-ester is added, and N stands for the mole percent of the aromatic ortho-ester to be added based on the total acid components constituting the polyester.

8. The improvement according to claim 1, wherein the amount of the aromatic ortho-ester to be added at one time is N' mole % expressed by the following formula $$0.1 \times [\eta]^{-1.3} \leq N' \leq 1 \times [\eta]^{-1.3}$$

wherein [$\eta$] designates the intrinsic viscosity, as calculated from the value measured in orthochlorophenol at 35°C., of the polyester at the time when the aromatic ortho-ester is added, and N' stands for the mole percent of the aromatic ortho-ester to be added based on the total acid components constituting the polyester.

9. The improvement according to claim 1, wherein the acid component is selected from at least one of the group consisting of aromatic dibasic acids, their functional derivatives, aromatic hydroxycarboxylic acids and their functional derivatives, and the glycol component is selected from at least one of the group consisting of 1,2-glycol and 1,4-glycol.

10. The improvement of claim 9 in which the intrinsic viscosity is at least 0.3.

* * * * *

UNITED STATES PATENT AND TRADEMARK OFFICE
CERTIFICATE OF CORRECTION

PATENT NO. : 3,984,379
DATED : October 5, 1976
INVENTOR(S) : OKA, ET AL.

It is certified that error appears in the above-identified patent and that said Letters Patent are hereby corrected as shown below:

Claim 1, column 56, line 4, delete "$R^7$", insert -- $R_7$ --
Claim 1, column 56, line 12, delete "$R^3$", insert -- $R_3$ --
Claim 6, line 2, delete "R7", insert -- $R_7$ --
Claim 7, line 6, delete "[72]", insert -- [n] --

Signed and Sealed this

Fourteenth Day of December 1976

[SEAL]

Attest:

RUTH C. MASON
*Attesting Officer*

C. MARSHALL DANN
*Commissioner of Patents and Trademarks*